United States Patent [19]

Cherif-Cheikh

[11] Patent Number: 5,595,760
[45] Date of Patent: Jan. 21, 1997

[54] SUSTAINED RELEASE OF PEPTIDES FROM PHARMACEUTICAL COMPOSITIONS

[75] Inventor: Roland Cherif-Cheikh, Issy-les-Moulineaux, France

[73] Assignee: Delab, Paris, France

[21] Appl. No.: 400,610

[22] Filed: Mar. 8, 1995

[51] Int. Cl.$^6$ .................................................. A61K 9/20
[52] U.S. Cl. ...................... 424/464; 424/422; 424/484; 424/488
[58] Field of Search ................................ 424/464, 422, 424/423, 484, 488

[56] References Cited

U.S. PATENT DOCUMENTS

| | | | |
|---|---|---|---|
| 3,773,919 | 11/1973 | Boswell et al. | 424/19 |
| 5,134,122 | 7/1992 | Orsolini | 424/489 |
| 5,225,205 | 7/1993 | Orsolini | 424/489 |
| 5,279,608 | 1/1994 | Cherig Cheikh | 604/892.1 |

FOREIGN PATENT DOCUMENTS

| | | | |
|---|---|---|---|
| 0139286 | 5/1985 | European Pat. Off. | A61K 9/00 |
| 0230647 | 8/1987 | European Pat. Off. | |
| 0403032 | 12/1990 | European Pat. Off. | |
| 0510913 | 10/1992 | European Pat. Off. | A61K 37/30 |
| 94/08623 | 4/1994 | WIPO | |
| 94/22423 | 10/1994 | WIPO | |
| 95/22314 | 8/1995 | WIPO | |

OTHER PUBLICATIONS

Search Report, Mar. 1996, WOX.
Database WPI, Section Ch, Week 9242, Derwent Publications Ltd., London, GB; Class B04, An 92-124827 & JP-A-04 244 031, (ZH Kankoku Kagaku Gijutsu Kenk), 1 Sep. 1992 (See Abstract).
Eckhardt et al., "Effect of Freezing on Aggregation of Human Growth Hormone", Pharm. Res. 8:1360-64 (1991).
Powell et al., "Peptide Liquid Crystals: Inverse Correlation of Kinetic Formation . . . ", Pharm. Res. 9:1352-54, (1994).
Wan et al., Pharm. Res. 11 (Supp. 10); Abstracts: PDD 7275 at p. S-243, and PDD 7466 at p. S-291 (1994).

*Primary Examiner*—Thurman K. Page
*Assistant Examiner*—Kathryne E. Shelborne
*Attorney, Agent, or Firm*—Fish & Richardson P.C.

[57] ABSTRACT

The invention features a method of administering a peptide to a patient and delivering the peptide continuously over an extended period of time of at least three days by obtaining a solid pharmaceutical composition including a soluble, gelable salt of the peptide and up to 30 percent, by weight, of a pharmaceutically acceptable, soluble, monomeric carrier, and parenterally administering the solid composition to the patient in one injection, wherein the solid composition automatically forms a gel after interaction with the patient's bodily fluids and releases the peptide continuously within the patient over an extended period of at least three days.

22 Claims, 18 Drawing Sheets

SUSTAINED RELEASE OF PEPTIDES FROM PHARMACEUTICAL COMPOSITIONS

FIELD OF THE INVENTION

This invention relates to the parenteral administration of sustained-release peptide compositions.

BACKGROUND OF THE INVENTION

Peptides are generally administered parenterally, e.g., by subcutaneous injection, since they are often degraded in the gastrointestinal tract.

Many peptide treatments (e.g., insulin, LHRH, and somatostatin) require either the continuous or repeated administration of the peptide in the patient over an extended period of time. However, such continual injections cause both inconvenience and discomfort to the patient.

Sustained-release formulations have been developed to deliver peptides over prolonged periods of time without the need for repeated injections. Solid polymeric microcapsules and matrixes, for example, utilizing biodegradable polylactic polymers, have been developed. See e.g., Hutchinson, U.S. Pat. No. 4,767,628 and Kent, et al., U.S. Pat. No. 4,675,189. Hydrogels have also been used as sustained-release formulations for peptides. These hydrogels comprise polymers such as poly-N-isopropyl acrylamide (NIPA), cellulose ether, hyaluronic acid, lecithin, and agarose to control the delivery. See, e.g., PCT Applications WO 94/08623.

Some peptides have been reported to form soluble aggregates or insoluble particulates once mixed into a solution. See, Eckhardt, et al., *Pharm. Res.*, 8:1360 (1991). Recently, others have studied the possibility of utilizing these peptide aggregates as sustained-release formulations. See European Patent Application 0510913 A2 (1992); and Wan, et al., *Pharmaceutical Research*, Vol. 11, 10 Suppl., abstracts P. S291 and P. S243 (1994). However, these aggregate sustained-release compositions require that the peptide be dissolved in saline or biologically compatible buffers, and then incubated until a liquid crystalline gel structure is formed.

SUMMARY OF THE INVENTION

The present invention provides pharmaceutical compositions which are administered to a patient to automatically form a sustained-release gel within the patient without the need for any extemporaneous dissolution or incubation of the composition. The invention is based on the discovery that certain soluble peptide salts can be formulated as parenteral sustained-release gel formulations without the addition of a biodegradable polymer or other carrier matrix to control the peptide's release profile. The new peptide compositions automatically gel upon interaction with a patient's bodily fluids, and then release the peptide continuously over an extended period of time. The new peptide compositions thus reduce the volume, cost, and manufacturing time of known sustained-release polymer-peptide formulations.

In general, the invention features a method of administering a peptide to a patient and delivering the peptide continuously over an extended period of time of at least three days by obtaining a solid pharmaceutical composition including a soluble, gelable salt of the peptide and up to 30 percent, by weight, of a pharmaceutically acceptable, soluble, monomeric carrier, e.g., mannitol, sorbitol, or lactose, and parenterally administering the solid composition to the patient in one injection, e.g., intramuscular, subcutaneous, intradermal, or intraperitoneal, wherein the solid composition automatically forms a gel after interaction with the patient's bodily fluids and releases the peptide continuously within the patient over an extended period of at least three days.

As used herein, a "gelable peptide salt" is a peptide salt which will form a gel upon contact with bodily fluids. Whether a peptide salt is "gelable," and will have the desired biological properties, can be determined by testing the peptide salt in the in vitro and in vivo assays described below. The term "peptide" means a natural or synthetic molecule comprising two or more amino acids linked by the carboxyl group of one amino acid and the amino group of another. Thus, the term includes both polypeptides and proteins. A "soluble" peptide salt is one having a solubility of 0.1 mg/ml, and preferably 1.0 mg/ml, in water at a pH of 7.0 and a temperature of 25° C.

The terms "biologically active analog" and "analog" are used interchangeably herein to cover naturally occurring, recombinant, and synthetic peptides, or derivatives or fragments of peptides, that exhibit substantially the same agonist or antagonist effect of unmodified, or naturally occurring peptides, e.g., those in which the N- or C- terminal group has been structurally modified.

Suitable peptides that can be used in the invention include growth hormone (GH), growth hormone releasing peptide (GHRP), growth hormone releasing factor (GRF), epidermal growth factor, interferon, insulin, somatostatin, bombesin, calcitonin, calcitonin gene related peptide (CGRP), amylin, parathyroid hormone (PTH), parathyroid hormone related peptide (PTHrp), gastrin, gastrin releasing peptide (GRP), melanocyte stimulating hormone (MSH), adrenocorticotrophic hormone (ACTH), luteinizing hormone (LH), luteinizing hormone-releasing hormone (LHRH), cytokinases, sorbine, cholecystokinin (CCK), glucagon, glucagon-like peptide (GLP), gastrin, enkephalin, neuromedin, endothelin, substance P, neuropeptide Y (NPY), peptide YY (PYY), vasoactive intestinal peptide (VIP), pituitary adenylate cyclase activating polypeptide (PACAP), bradykinin, thyrotropin releasing hormone (TRH), beta-cell tropin (a fragment of ACTH), or biologically active analogs of any of the foregoing.

Preferred soluble, gelable peptide salts according to the invention include salts of somatostatin and analogs such as SOMATULINE™ (BIM 23014C) (Kinerton, Ltd., Dublin, Ireland; see, e.g., Johnson et al., *Eur. J. Endocrinol.* 130:229–34, 1994), salts of calcitonin and its analogs, salts of LHRH analogs such as the antagonist GANIRELIX™ (GRX; see, e.g., Nestor et al., *J. Med. Chem.*, 35(21):3942–3948, 1992), and salts of GH, GRF, PTH, PTHrp, and biologically active analogs thereof.

Examples of preferred salts are those with therapeutically acceptable organic acids (e.g., acetic, lactic, maleic, citric, malic, ascorbic, succinic, benzoic, methanesulfonic, or toluenesulfonic, and salts with inorganic acids such as the hydrohalic acids (e.g., hydrochloric acid), sulfuric acid, or phosphoric acid.

The gelable peptides of the invention can be compounded with a pharmaceutically acceptable, monomeric, soluble carrier for ease of manufacture and/or administration. Examples of carriers include polyalcohols such as mannitol and sorbitol, sugars such as glucose and lactose, surfactants, organic solvents, and polysaccharides.

Solid compositions of the invention can be manufactured in the form of a cylinder with a diameter of less than 3 mm, and preferably less than 2 mm, for administration by standard trocar, and the gel preferably releases the peptide continuously over a period of at least 14 days, and preferably at least 30 days.

A semisolid suspension can also be used in the method of the invention. The terms "semisolid suspension" and "semisolid composition" are used interchangeably herein to refer to viscous, paste-like suspensions of peptide salts in a liquid solvent, such as sterilized water. A semisolid suspension according to the invention includes (1) a solid, soluble, gelable peptide salt and up to 30 percent, by weight, of a pharmaceutically acceptable, soluble carrier; and (2) a solvent, e.g., an aqueous solvent like sterilized water, in an amount less than 50 percent, and preferably 20 or 10 percent, of the amount of solvent required to dissolve the peptide salt and to provide the semisolid consistency. The suspension is also parenterally administered to the patient in one injection, and automatically forms a gel after interaction with the patient's bodily fluids.

The amount of solvent, e.g., water, in the suspension must be less than what can dissolve all of the peptide salt, i.e., the ratio of peptide to solvent must be greater than the peptide's solubility, e.g., 26.0 mg/ml for the somatostatin analog SOMATULINE™ in water, at a pH of 7.0 and a temperature of 25° C.

The invention further features a sustained-release gel formed within a patient. The gel is made of a pharmaceutical composition including a soluble, gelable peptide salt and up to 30 percent, by weight, of a pharmaceutically acceptable, soluble carrier, and one or more bodily fluids of the patient, wherein the peptide salt automatically forms the gel after interaction with the bodily fluids, and the gel releases the peptide continuously within the patient over a period of at least three days after formation. The pharmaceutical composition that forms the gel can be a solid, or it can further include a solvent, e.g., sterilized water, in an amount less than 50 percent of the amount of solvent required to dissolve the peptide salt and to provide the pharmaceutical composition with a semisolid consistency.

In addition, the invention features a solid, non-particulate, sustained-release pharmaceutical composition for parenteral administration to a patient. This composition consists essentially of (1) a soluble, gelable peptide salt, and (2) up to 30 percent, by weight, of a pharmaceutically acceptable, monomeric, soluble carrier, compounded into a solid cylindrical form, wherein the solid composition automatically forms a gel after interaction with the patient's bodily fluids, and releases the peptide continuously within the patient over an extended period of at least three days.

The invention also features a semisolid, sustained-release pharmaceutical suspension for parenteral administration to a patient. This suspension consists essentially of (1) a soluble, gelable peptide salt and up to 30 percent, by weight, of a pharmaceutically acceptable, soluble carrier; and (2) a solvent in an amount less than 50 percent, and preferably 20 or 10 percent, of the amount of solvent required to dissolve the peptide salt and to provide the semisolid consistency of the suspension, wherein the semisolid suspension automatically forms a gel after interaction with the patient's bodily fluids, and releases the peptide continuously within the patient over an extended period of at least three days.

In another aspect, the invention features a method of making a solid pharmaceutical composition by a) mixing a soluble, gelable peptide salt and up to 30 percent, by weight, of a pharmaceutically acceptable, soluble carrier to form a mixture; b) compounding the mixture with a liquid vehicle to form a semisolid formulation; c) extruding the semisolid formulation to form an elongated filament; d) cutting the elongated filament into semisolid cylindrical rods; and e) drying the semisolid rods to form solid cylindrical rods. Preferably, the solid rods have a diameter of less than 2 or 3 mm.

In another embodiment, the invention features an injection system for the administration of a semisolid, sustained-release pharmaceutical suspension. This system includes a) a first syringe having a hollow barrel with two ends and a nozzle at the first end, and a plunger slidably arranged within the barrel and extending out of the barrel through an opening in the second end of the barrel, wherein the barrel contains a soluble, gelable peptide salt between the nozzle and the plunger; b) a second syringe having a hollow barrel with two ends and an outlet nozzle at the first end, and a plunger slidably arranged within the barrel and extending out of the barrel through an opening in the second end of the barrel, wherein the barrel contains a pharmaceutically acceptable liquid carrier between the outlet nozzle and the plunger; c) a connector having a liquid conduit, the connector detachably connecting the nozzle of the first syringe with the outlet nozzle of the second syringe and permitting liquid communication from the outlet nozzle to the nozzle; and d) a temporary sealing membrane positioned within the second syringe to separate the liquid carrier from the gelable peptide salt in the first syringe, wherein sufficient force applied to the plunger in the second syringe causes the liquid carrier to break the temporary sealing membrane allowing the liquid carrier from the second syringe to flow through the connector and into the first syringe to mix with the gelable peptide salt to form a semisolid, sustained-release pharmaceutical suspension.

Unless defined otherwise, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, and other references mentioned herein are incorporated by reference. In addition, the materials, methods, and examples are illustrative only and not intended to be limiting.

Other features and advantages of the invention will be apparent from the detailed description, and from the claims.

DETAILED DESCRIPTION

Figure 1:
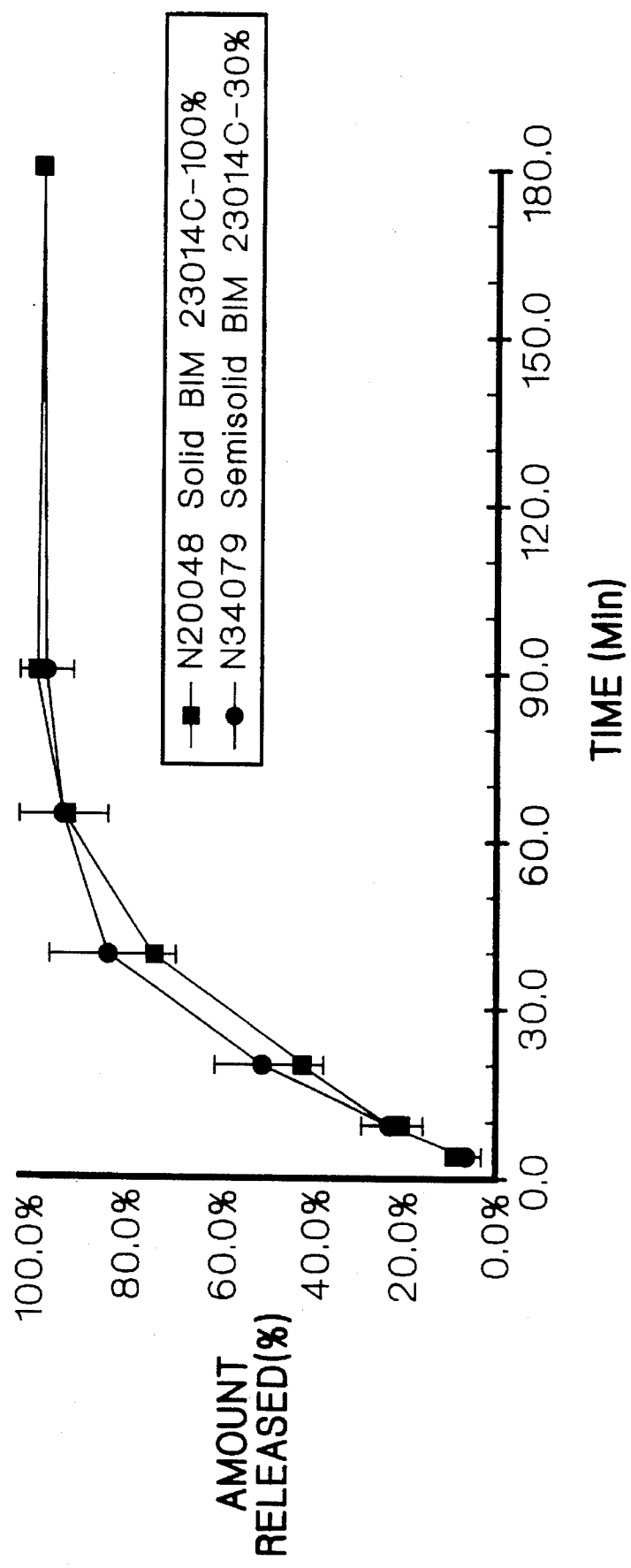
FIG. 1 is a graph comparing the release rate and delivery profile of solid and semisolid drug compositions in vitro.

The invention relates to pharmaceutical compositions, e.g., solid cylinders or semisolid suspensions, that automatically form sustained-release gels once administered to a patient, and new syringe-like devices designed to administer the new compositions. The syringe-like devices are used to administer the semisolid suspensions. Standard trocars are used to administer the solid compositions.

Each unit of the new compositions will contain at least the daily dose of the peptide multiplied by the desired number of days of activity. After the composition automatically gels upon contact with bodily fluids, the peptide is delivered from the gel according to a blood level profile that is comparable to the blood level profile of the peptide when administered by continuous daily injection, by known sustained-release compositions, e.g., polymeric peptide formulations, or by an infusion pump operating under a steady mode of delivery.

Peptides Suitable for Pharmaceutical Compositions

The salt form of the peptides that can be used in the compositions of the invention must gel in bodily fluids, e.g., lymph or blood serum, when administered to a patient, and, once gelled, are capable of controlling the delivery of the peptide at a rate suitable for a therapeutic use of the drug. For instance, as demonstrated in the examples below, gels of somatostatin analogs such as SOMATULINE™, at sufficient dosages, are able to maintain a sustained release of at least 1.0 ng/ml of the peptide in the blood for over one month. This amount is the therapeutic level of somatostatin required for treating, e.g., acromegaly.

Peptides that are preferred for use in the new compositions include somatostatin, calcitonin, parathyroid hormone (PTH), parathyroid hormone related protein (PTHrP), soluble agonists or antagonists of LHRH, GRF, and other soluble analogs that have the agonist or antagonist effect of any of these peptides. Preferably, the peptide comprises at least one hydrophobic residue, e.g., non-naturally occurring residues such as napthylalanine (Nal), norleucine (Nle), and halogen substituted phenylalanines, and naturally occurring residues such as Trp, Ile, Phe, Val, Leu, Met, Ala, Gly, or Cys, that allow the peptide to better form a gel. Hydrophobicities of amino acids can be determined as discussed in Eisenberg, *Ann. Rev. Biochem.*, 53:595–623 (1984).

The configuration of the peptide is also preferably altered, e.g., by a D- amino acid to decrease enzymatic degradation, by a disulfide bridge to create a cyclic peptide, or by an internal amide bond between the side chains of two amino acid residues. These features of suitable peptides are believed to allow or enhance the ability of the peptide salt to automatically form a gel once administered to a patient.

The following publications disclose the sequences of PTH peptides and analogs: John P. Bilezikian (ed.), *The Parathyroids Basic and Clinical Concepts*, pages 239–258 (Raven Press, N.H. 1994); Nissenson et al., "Structure & Function of the Receptor for Parathyroid Hormone and Parathyroid Hormone-Releasing Hormone," *Receptor*, 3:193–202 (1993); Bachem California 1993–1994 Catalog (Torrance, Calif.); and SIGMA®, Peptides and Amino Acids 1994 Catalog (St. Louis, Mo.).

The following publications disclose the sequences of PTHrP peptides and analogs: Yasuda, et al., *J. Biol. Chem.*, 264:7720–7725 (1989); and Burtis, W. J., *Clin. Chem.*, 38(11):2171–2183 (1992). More examples can be found in the following publications: PCT Application 94/01460 (1994); PCT Application 94/02510 (1994); PCT Application 93/20203 (1993); PCT Application 92/11286 (1992); PCT Application 93/06846 (1993); PCT Application 92/10515 (1992); PCT Application 92/00753 (1992); EP Application 477885 A2 (1992); EP Application 561412 A1 (1993); EP Application 451867 A1 (1991); German Application 4203040 A1 (1993); U.S. Pat. No. 4,771,124 (1988); U.S. Pat. No. 4,656,250 (1987); U.S. Pat. No. 5,229,489 (1993); and Bachem California 1993–94 Catalog, 30–34 (1993).

The following publications disclose the sequences of somatostatin analogs: PCT Application WO 91/09056 (1991); EP Application 0 505 680 A1 (1992); EP Application 0 363 589 A2 (1990); EP Application 0 203 031 A2 (1986); U.S. Pat. No. 4,904,642 (1990); U.S. Pat. No. 4,871,717 (1989); U.S. Pat. No. 4,853,371 (1989); U.S. Pat. No. 4,725,577 (1988); U.S. Pat. No. 4,684,620 (1987); U.S. Pat. No. 4,650,787 (1987); U.S. Pat. No. 4,603,120 (1986); U.S. Pat. No. 4,585,755 (1986); U.S. Pat. No. 4,522,813 (1985); U.S. Pat. No. 4,486,415 (1984); U.S. Pat. No. 4,485,101 (1984); U.S. Pat. No. 4,435,385 (1984); U.S. Pat. No. 4,395,403 (1983); U.S. Pat. No. 4,369,179 (1983); U.S. Pat. No. 4,360,516 (1982); U.S. Pat. No. 4,358,439 (1982); U.S. Pat. No. 4,328,214 (1982); U.S. Pat. No. 4,316,890 (1982); U.S. Pat. No. 4,310,518 (1982); U.S. Pat. No. 4,291,022

(1981); U.S. Pat. No. 4,238,481 (1980); U.S. Pat. No. 4,235,886 (1980); U.S. Pat. No. 4,224,190 (1980); U.S. Pat. No. 4,211,693 (1980); U.S. Pat. No. 4,190,648 (1980); U.S. Pat. No. 4,146,612 (1979); U.S. Pat. No. 4,133,782 (1979); Van Binst et al., *Peptide Res.*, 5:8 (1992); Prevost et al., *Cancer Res.*, 52:893 (1992); and Bachem California 1993–1994 Catalog 94–95 (1993).

The following publications disclose the sequences of GRF analogs: PCT Application WO 91/18998 (1991); PCT Application WO 92/18537 (1992); PCT Application WO 92/00095 (1992); PCT Application WO 91/03053 (1991); EP Application 314866 A2 (1989); EP Application 136475 B1 (1991); EP Application 320785 A2 (1989); U.S. Pat. No. 4,732,972 (1988); U.S. Pat. No. 4,627,312 (1986); EP Patent Application 511003 A1 (1992); and Bachem California 1993–1994 Catalog 64–65 (1993).

The following publications disclose the sequences of LHRH analogs: U.S. Pat. No. 4,307,083; U.S. Pat. No. 4,292,313; U.S. Pat. No. 4,124,577; U.S. Pat. No. 4,111,923; U.S. Pat. No. 4,101,538; U.S. Pat. No. 4,101,537; U.S. Pat. No. 4,093,611; U.S. Pat. No. 4,087,419; U.S. Pat. No. 4,087,418; U.S. Pat. No. 4,087,417; U.S. Pat. No. 4,083,967; U.S. Pat. No. 4,062,835; U.S. Pat. No. 4,031,072; U.S. Pat. No. 4,031,070; U.S. Pat. No. 4,031,069; U.S. Pat. No. 3,824,227; U.S. Pat. No. 3,824,065; Rivier et al., *J. Med. Chem.*, 29:1846 (1986); Ljungquist et al., *Proc. Natl. Acad. Sci., USA*, 85:8256 (1988); Coy et al., *Amer. Clin. Res.*, 10:139 (1978); Sundaram et al., *Life Sci.*, 28:83 (1981); Rivier et al., *Life Sci.*, 23:869 (1978); Humphrey et al., *J. Med. Chem.*, 21:120 (1978); and Bachem California 1993–1994 Catalog 67–68 (1993).

The following publications disclose the sequences of calcitonin analogs: EP Application 464549 A1 (1992) and Bachem California 1993–1994 Catalog 28 (1993).

In Vitro Assays for Suitable Peptide Salts

A simple in vitro assay can be used to determine the suitability of a given peptide salt for use in the present invention. The peptide salt, e.g., in the form of a powder or a suspension, is mixed with a clear bodily fluid, e.g., lymph, plasma, or serum, in a container. This container is heated to 37° C. e.g., by a water or oil bath A visual inspection is made to determine whether the peptide salt formed a gel.

An in vitro light diffraction assay can also be used to determine whether a peptide salt will be suitable for use in the present invention. The peptide salt, e.g., in the form of a powder, is mixed on a glass microscope slide with between 20 and 50 percent, by weight, of water. After the peptide is well mixed, e.g., after 5 minutes, the slide is analyzed on an inverted microscope, such as the ZEISS® AXIOVERT 100, using polarized light. If the polarized light is diffracted, as indicated by the presence of bright colors, the peptide salt has formed a gel, and is suitable for use in the present invention.

Another in vitro assay was used to study the release characteristics of the solid and semisolid compositions of the invention. The MICROETTE™ transdermal diffusion cell (Hanson Research, Palo Alto, Calif.) was utilized in the assay as an autosampling system composed of six thermostatic cells, a mechanical stirring device, and a sample collector.

When used to study the delivery profile of solid SOMATULINE™ cylinders, the assay conditions for the autosampling system were as follows: release medium=NaCl 0.9%, initial volume=7 ml, rod weight=1.6 to 1.8 mg., temperature=37° C., stirring rate=60 rpm, final stirring rate=400 rpm (for the last 15 min.), and replacement volume=481 µl. Samples were taken at 4, 10, 20, 40, 65, 90, 180 and 270 minutes.

The samples collected in the autosampler were analyzed by high pressure liquid chromatography (HPLC) and quantified in a Hewlett Packard Series 1090 Liquid Chromatograph (Teknokroma, Barcelona, Spain) with automatic injector. A UV-VIS Diode Array detector was used for the analysis. A NUCLEOSIL™ C-18 column, 25 cm×4.0 mm diameter, was used. The assay conditions for the HPLC were as follows: Component A=0.1% TFA in AcCN:Water (80:20); Component B=0.1% TFA in water; flow=0.9 ml/min.; injection volume=20 µl; temperature=room temperature; detection=UV–280 nm; and acquisition time=20 minutes. The retention time of SOMATULINE™ was calculated to be 14 minutes. The gradient system used for the HPLC are depicted in Table I.

TABLE I

| Time (minutes) | % Component A | % Component B |
|---|---|---|
| 0 | 25 | 75 |
| 17 | 69.2 | 30.8 |
| 19 | 25 | 75 |
| 25 | 25 | 75 |

In Vivo Assay of Sustained Peptide Release

Once a particular peptide salt is found to gel in any of the in vitro assays described above, an in vivo assay can be used to determine the suitability of that peptide salt for therapeutic use in animals or humans. A blood level release profile for a particular peptide salt can be determined by injecting the peptide salt into an animal, e.g., a Sprague Dawley rat or dog, and testing blood samples taken at specific time intervals, e.g., hourly intervals over 1 to 5 days, or 12 or 24 hour intervals over 5 to 45 days, for the concentration of the peptide. The suitability of a particular peptide gel, or a peptide/carrier gel, for therapeutic delivery of the peptide can thus be determined.

Specifically, animals are anaesthetized with pentobarbital (60 mg/kg i.p. for rats), and a jugular vein is cannulated for blood sampling. A test peptide semisolid suspension or solid composition (or standard solution for comparison purposes), e.g., of SOMATULINE™, is injected subcutaneously at a specific dosage, e.g., 1.0, 3.0, or 6.0 mg/kg of SOMATULINE™. After administration of the peptide composition or solution, heparinized blood samples are obtained through the cannula at set time intervals, and plasma is separated after centrifugation. The amount of peptide in the plasma samples is determined by a standard radioimmunoassay (RIA) technique that allows a direct measurement without extraction of the peptide from the rat plasma. The resulting data is plotted (blood concentration (ng/ml) vs. time) to establish a blood level release profile.

In addition, the presence of the peptide in the animal can be determined indirectly by assaying for any biological response of the animal to the peptide. For example, if the peptide is a somatostatin analog, its effect, and thus presence, can be determined by assaying the inhibition of growth hormone release in response to GRF using standard assays. Such indirect methods of determining the presence of a peptide can also be used in human patients.

When monitored for 1 to 3 days, this in vivo assay can be used to determine whether a particular peptide will form a gel once administered in vivo that provides the desired sustained-release of the peptide. A peptide is suitable for the present invention if it provides a sustained-release of the peptide, e.g., at therapeutic levels, for at least 3 days.

This assay can also be used to determine the effectiveness of a particular peptide salt or combination of salt and carrier, and the necessary dosages, for use in a specific therapy for a particular animal, by comparing the blood level release profile to known dosage requirements for a particular peptide and a particular disease. For example, it is known that a blood concentration of 1.0 ng/ml of a somatostatin analog must be continuously sustained to treat acromegaly. Likewise, this assay can be used to estimate the expected effectiveness of a particular type and dosage of a peptide salt for use in specific human therapies.

Carriers Suitable for Pharmaceutical Compositions

Although certain gelable peptide salts, e.g., salts of SOMATULINE™, can be formulated into a solid composition without the need for any carrier, the compositions of the invention also can be manufactured using carriers that are homogeneously compounded with the peptides. The carrier should be water-soluble, monomeric, and directly eliminated by the body. Preferably, the carrier has a molecular weight of less than 1000 daltons. The carrier is chosen to give the composition its physical characteristics, but does not typically affect the sustained-release characteristics of the compositions. However, as demonstrated below, certain carriers can be used to decrease or increase both the release rate and the duration of delivery of the compositions.

Suitable carriers include surfactants, e.g., TWEEN® 80, polyalcohols, e.g., mannitol and sorbitol, monosaccharides, e.g., lactose and glucose, organic solvents, and polysaccharides.

Method of Preparing Solid Pharmaceutical Compositions

The manufacturing process of the invention avoids solubility problems of many peptides since there is no need to dissolve the peptide prior to injection. Another advantage of the solid compositions of the invention is their stability. The anhydrous, solid compositions of the invention avoid the problems of degradation, crystallization, aggregation, and coagulation associated with hydrated sustained-release formulations such as hydrogels.

One method for mixing a peptide and a carrier, and loading the resulting drug composition for injection via a trocar needle is as follows.

The carrier, e.g., mannitol, is dissolved in a liquid manufacturing vehicle, e.g., water or an organic solvent. The resulting solution is mixed with the desired peptide to form a homogeneous semisolid mixture. If the final solid composition does not include a carrier, then the peptide is mixed solely with water or another liquid vehicle to form a semisolid mixture.

The semisolid mixture is then transferred to an extrusion chamber, e.g., a stainless syringe or a feeding extrusion area, with an plunger or a screw, and an extrusion nozzle with a 0.5 to 3.0 mm internal diameter. The mixture is extruded, cut into rods of a precise length, and collected. The resulting rods are thoroughly dried in a vacuum and preferably have a final diameter of 2 or 3 mm. Various known techniques can be used to move the non-solid mass of material through the orifice to produce the elongated rods with a desired cross-section once dried.

The manufacturing vehicle can be removed by evaporation, freeze-drying, or vacuum drying. The rods are then tested to determine the precise mass percentage of peptide, i.e., dosage per unit length of cylinder. Five cylinders are taken from a batch, weighed, and then processed to remove the total amount of peptide, e.g., by solubilization in an appropriate solvent such as 0.1% acetic acid in water. The amount of extracted peptide is measured using standard HPLC methodology as used in the in vitro assay described above.

Prior to use, the rods are also tested for uniformity by calculating their weight/length ratio. The lengths and weights of five cylinders are measured and the ratio of length to weight is calculated. This control is positive only if the relative standard deviation (RSD) is less than 5%. This RSD equals $[SD_{length/weight\ ratio}/Mean_{length/weight\ ratio}] \times 100$, so it is a measure of the uniformity of the length/weight ratio.

Once the rods have been accepted, the dosage is determined by length and weight measurement. Having already calculated the peptide concentration, the rods are cut into precise lengths corresponding to desired dosage units. The rods are tested once more prior to administration by weighing them on a balance. The rods are then ready to be loaded into hollow needles, e.g., of a trocar.

Trocar needles are loaded through the back end after the tip of the needle is sealed, e.g., with a cap. The back end of the needle preferably has a funnel shape, which makes it easy to insert the solid rods. A metallic plunger then pushes the rod out of the tip of the needle and into a patient.

In a preferred embodiment, the back end of the trocar needle is attached to a sterile stainless steel, plastic, or glass cylinder into which a semisolid composition is extruded, cut, and dried. The cylinder is situated such that when dried, the rod falls into the needle by gravity. The pre-loaded trocar needle is then ready to be connected with its metallic plunger system and its activating system to a standard trocar.

Method of Preparing Semisolid Suspensions and Freeze-Dried Compositions

Semisolid suspensions can be made using the same peptides and carriers used to make the solid compositions. However, compared to the solid compositions, the semisolid peptide suspensions are hydrated with between 10 and 90%, by weight, of an aqueous solvent (e.g., sterilized water) to form highly viscous or paste-like compositions. Preferably the water is added just prior to administration of the composition to a patient.

The semisolid suspensions can be manufactured by the same process as described above for solid compositions, i.e., by extrusion, but without the final vehicle removal step. The semisolid extruded rods can be directly injected into a patient with a syringe-like device, e.g., as described below. Alternatively, the dried, solid rods can be rehydrated to form a semisolid suspension prior to injection.

Semisolid compositions can also be manufactured by a freeze-drying process which simplifies the unit dosage control and allows simple sterilization before the composition is loaded into a needle. In this process, the peptide, with or without a carrier, is first dissolved in water. The resulting solution is sterilized by passage through a 0.22 micron filter under pressure, e.g., using a syringe with a plunger. Once filtered, the solution must be handled under sterile conditions. Volume is precisely controlled, e.g., with a micropipette, and the sterile solution is filled into a sealed syringe cylinder. The liquid in the cylinder is then freeze-dried. The resulting lyophilized solid volume is compacted, e.g., using a plunger, in the syringe under vacuum.

The syringe containing the compacted, sterile solid is then packaged under vacuum. The solid composition will remain stable in this condition for extended periods of time without need of refrigeration or other special storage conditions. The solid composition is hydrated with water just prior to administration, e.g., using the two-part device described below, which contains the requisite volume of sterile water in a separate syringe-like cylinder. The freeze-dried solid is rehydrated to form a viscous, semisolid suspension that can then be injected into a patient.

A solution of the peptide composition is undesirable, because such a solution, once injected, will disperse and not form the sustained-release gel of the invention. Thus, the amount of water is carefully selected to be less than that required to dissolve a specific amount of the peptide composition For example, at 25° C., pH 7.0, 1.0 ml or less of water is required when mixed with 26 mg of the acetate salt of SOMATULINE™ to avoid the formation of a solution. By using an amount of water that is less than 50 percent, and preferably less than 20 or 10 percent, of the amount of water required to dissolve a peptide salt, a semisolid or paste-like suspension, rather than a solution, is ensured.

In a preferred embodiment, a needle is attached to the syringe cylinder with a funnel shaped connector. The funnel shaped connector can be part of the needle or part of the syringe. The needle can be fixed on the syringe or attached to the syringe just prior to use. The needle is adapted, in length and outer diameter, to the injection route, e.g., intramuscularly, intradermally or subcutaneously. The inside surface of the needle is preferably smooth to aid the injection of the semisolid composition.

The syringe preferably has a plunger of small diameter (1 to 5 mm) so that the small volume of semisolid composition (10 μl to 300 μl) will represent a significant length in the syringe barrel. This allows more accurate visualization and dosage measurement.

COMPOSITION EXAMPLES

Example 1

100% SOMATULINE™ Solid Composition 140 mg of water was added to 60 mg of the acetate salt of the somatostatin analog SOMATULINE™ (Kinerton, Ltd., Dublin, Ireland). Unless otherwise noted, the acetate salt of SOMATULINE™ was used in the following examples listing SOMATULINE. The mixture was kneaded with a spatula in a 2 ml plastic syringe and subsequently added to a stainless steel syringe, having a chamber with an internal diameter of 5 mm and an extrusion head of 2.5 mm internal diameter. The mixture was extruded as thin filaments through the syringe using a syringe pump. The resulting extruded filaments were cut into 3 cm rods and collected on glass slides. The rods were then allowed to dry under vacuum for 24 hours. The resulting 1.4 mm diameter rods contained 10 mg of SOMATULINE™/cm. The rods were loaded into 3 cm long trocar needles with an internal diameter of 1.5 mm.

Example 2

80% SOMATULINE™, 20% Mannitol Solid Composition

The protocol of Example 1 was followed by first mixing 1 g of mannitol (Roquette, Lestrein, France) with 9 g of water to form a solution. 0.140 g of this solution was added to 0.060 g of SOMATULINE™. The extruded filaments were cut and collected on glass slides, and dried under vacuum for 24 hours. The resulting 2.9 cm rods contained 40 mg of SOMATULINE™ (20%, by weight, mannitol and 80%, by weight, SOMATULINE™).

Example 3

100% SOMATULINE™ Semisolid Suspension 700 mg of water was added to 300 mg of SOMATULINE™ to make a semisolid suspension. The mixture was kneaded with a spatula in a 5 ml plastic syringe. 200 mg of the semisolid composition (60 mg of peptide) was loaded into each syringe.

Example 4

80% SOMATULINE™, 20% Mannitol Semisolid Suspension 0.1125 mg of mannitol and 14.8875 g of water were mixed to form a carrier solution. 400 mg of SOMATULINE™ was dissolved in 14.60 g of this carrier solution. Then, 2.0 ml of the resulting solution was placed into individual plastic syringes and lyophilized. The resulting solid was compacted to a volume of 100 μl with a plunger. Just prior to administration, the solid composition was hydrated with 133.33 μl of water to form a semisolid suspension.

Example 5

90% SOMATULINE™, 10% Sorbitol Solid Composition

The protocol in Example 2 was followed by mixing 0.5 g of sorbitol (Roquette, Lestrein, France) and 9.5 g of water to form a solution. 0.140 g of this solution was added to 60 g of SOMATULINE™. The mixture was weighed, kneaded, and extruded. The extruded filaments were cut and collected on glass slides, and dried under vacuum for 24 hours. The resulting 2.5 cm rods contained 3.5 mg of SOMATULINE™ (10%, by weight, of sorbitol and 90%, by weight, of SOMATULINE™).

Example 6

84% SOMATULINE™, 16% TWEEN® 80 Solid Composition

The protocol of Example 2 was followed by mixing 0.8 g of TWEEN® 80 (Sigma, St. Louis Mo.) and 9.2 g of water to form an 8% carrier solution of TWEEN® in water. 140 mg of this carrier solution was added to 60 mg of SOMATULINE™. The mixture was weighed, kneaded, and extruded. The extruded filaments were cut and collected on glass slides, and dried under vacuum for 24 hours. The resulting 2.5 cm rods contained 3.5 mg of SOMATULINE™.

IN VITRO COMPARATIVE EXAMPLES

The following examples demonstrate the effect, or lack of effect, of various modifications of the solid and semisolid compositions of the invention.

Example 7

Comparisons of Solid and Semisolid Compositions

The in vitro protocol described above was used to determine whether there was any difference between the delivery profiles of a 100% SOMATULINE™ solid composition and a 30% SOMATULINE™ and 70% water semisolid suspension. Each composition comprised the same dose of SOMATULINE™. The results are shown in the graph of FIG. 1. No significant difference was observed between the two compositions.

Example 8

Effect of Carriers on Peptide Release Rate

The in vitro protocol described above was also used to determine the effect of different carriers on the delivery profile and release rate of different solid SOMATULINE™ compositions: (1) 100% SOMATULINE™, (2) 86% SOMATULINE™ and 14% TWEEN® 80, (3) 85% SOMATULINE™ and 15% hyaluronic acid, (4) 90% SOMATULINE™ and 10% sorbitol, and (5) 80% SOMATULINE™ and 20% mannitol. The results of these experiments are depicted in FIGS. 2 and 3.

Figure 2:
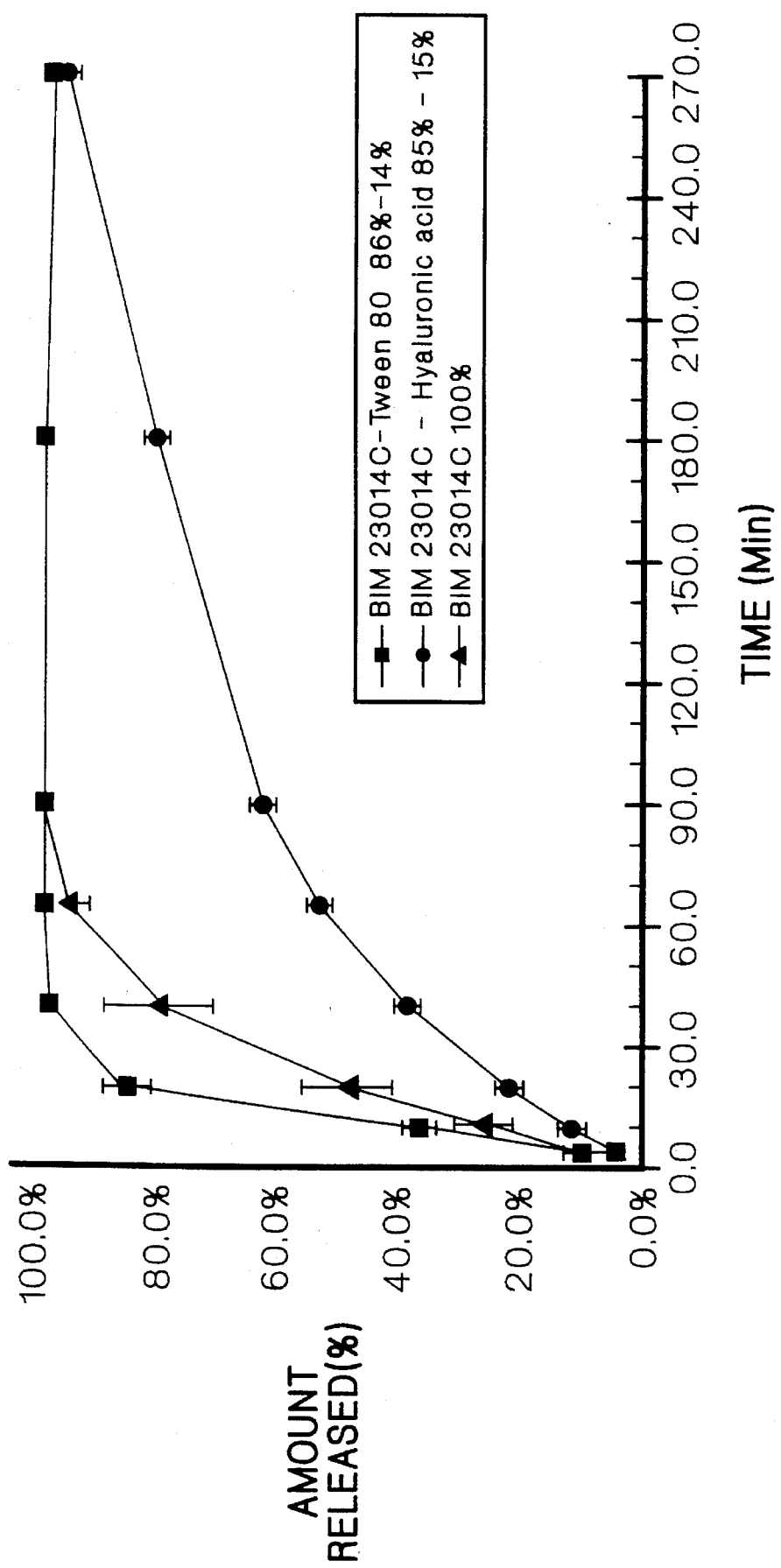
FIG. 2 is a graph showing the effect of the surfactant TWEEN® 80 and the carrier hyaluronic acid on the release rate and delivery profile of a peptide from a solid pharmaceutical composition in vitro.
Figure 3:
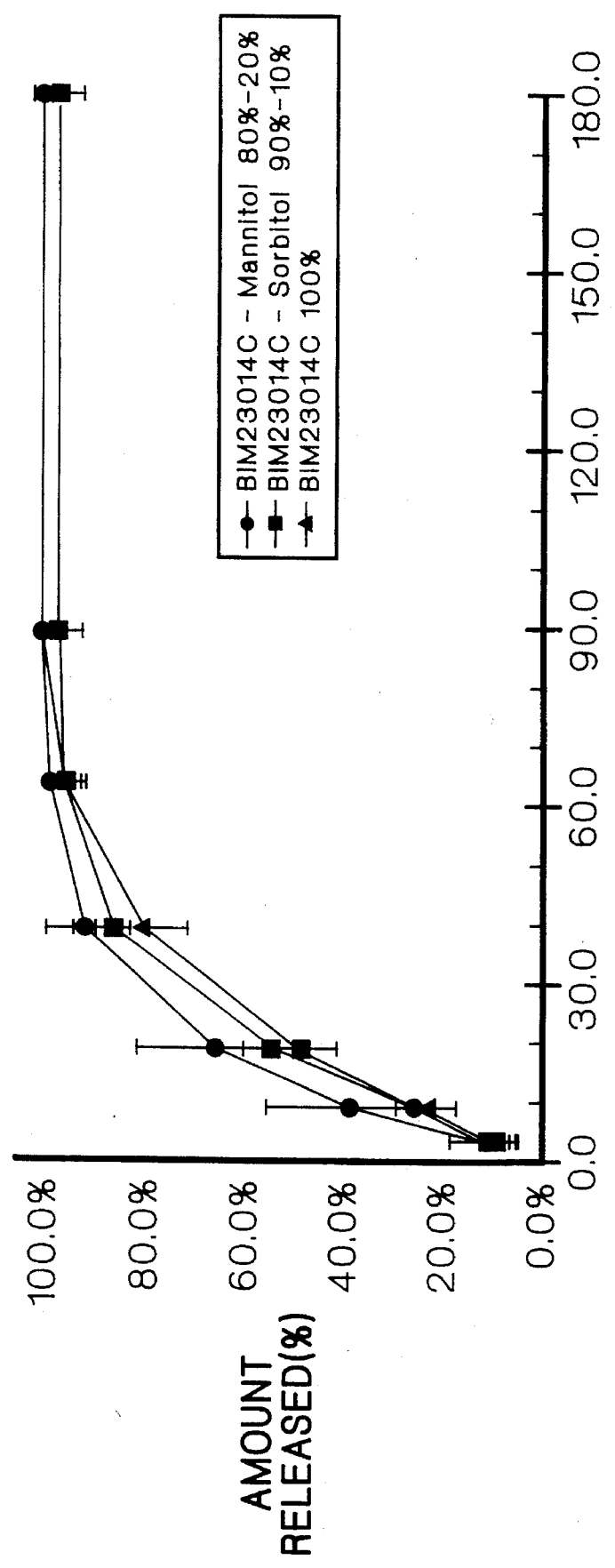
FIG. 3 is a graph showing the effect of monosaccharides on the release rate and delivery profile of a solid drug composition in vitro.

FIG. 2 shows that compared to 100% SOMATULINE™, hyaluronic acid decreases the delivery rate, while TWEEN™ 80 increases the delivery rate. FIG. 3 shows that compared to 100% SOMATULINE™, the monomeric soluble carriers mannitol and sorbitol provided only a slight increase in release rate.

Example 9

Figure 4:
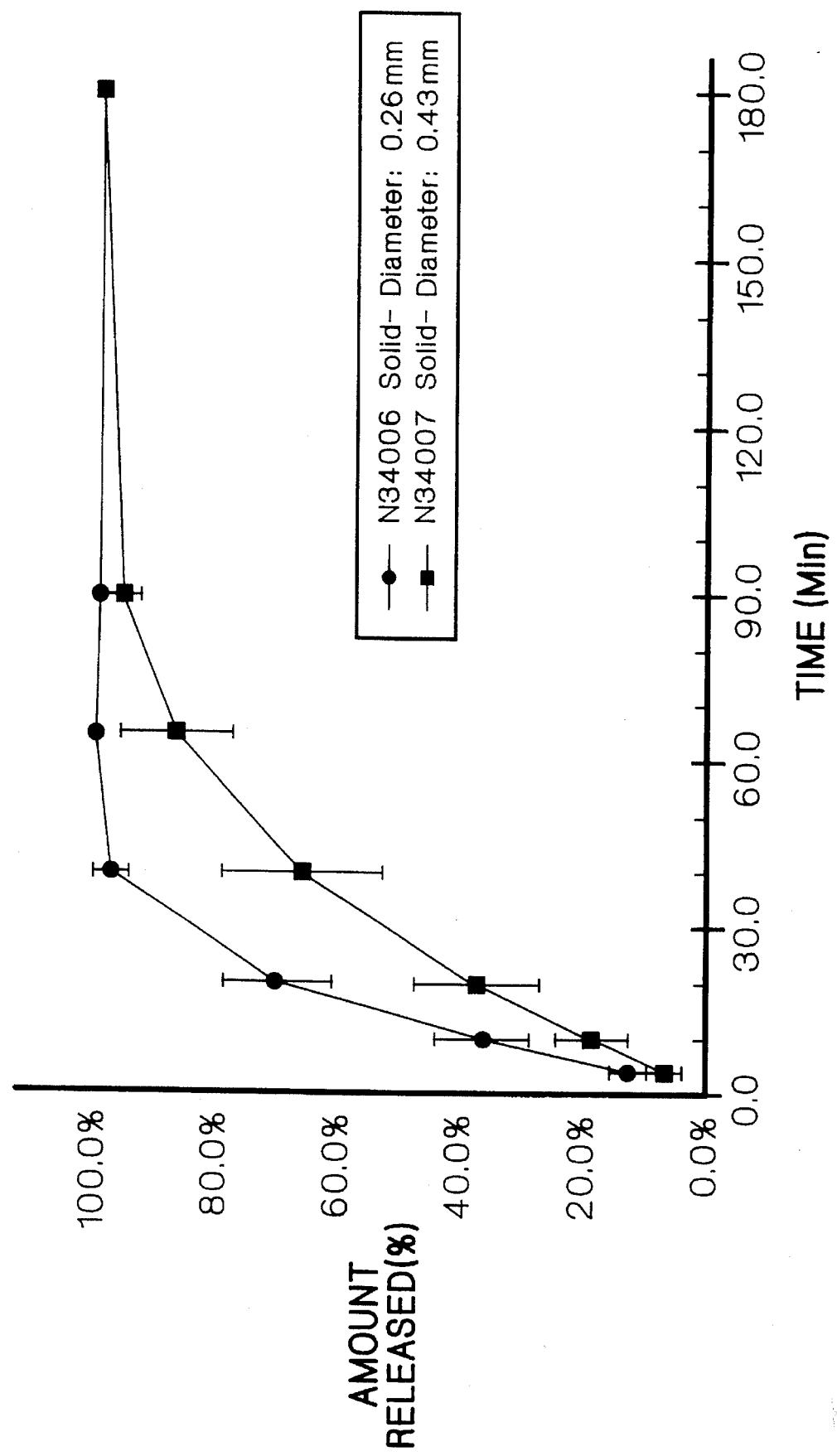
FIG. 4 is a graph showing the effect of varying diameter on the release rate and delivery profile of a solid drug composition in vitro.

Effect of Diameter of Solid Pharmaceutical Compositions on Peptide Release Rate The in vitro protocol described above was also used to determine the effect of rod diameter on the delivery profile and release rate of solid SOMATULINE™ compositions. The solid composition comprised a mixture of SOMATULINE™ and mannitol (80:20). Diameters of 0.26 mm and 0.43 mm were studied. The results on this assay are depicted in the graph of FIG. 4. The smaller diameter of 0.26 mm produced a faster in vivo release than the larger diameter of 0.43 mm. In addition, the smaller diameter rod provided complete release in less than half the time required for complete release by the larger diameter rod.

IN VIVO EXAMPLES

The animal test examples below demonstrate the pharmacokinetic delivery profiles of various solid and semisolid compositions of the acetate salt of the somatostatin analog SOMATULINE™ compared with standard liquid drug solutions.

Example 10

In Vivo Comparisons of Peptide Solutions vs. Gels Formed from Solid Peptide Compositions The in vivo assay described above was used to study the difference in blood level profiles resulting from injections of a standard solution of SOMATULINE™ compared to a 100% SOMATULINE™ solid composition according to the invention.

The solution was made from the peptide dissolved in physiological serum, and was injected subcutaneously at a dosage of 1.0 ml/kg and 0.5 mg/kg of SOMATULINE™. The rats were anaesthetized with pentobarbital (60 mg/kg i.p.) and the right jugular vein was cannulated for blood sampling. Following surgery, the rats were allowed to recover for two days prior to experimentation. The animals were housed in cages where they could freely move. After administration of the drug solution, heparinized blood samples were obtained through the cannula, and plasma was separated after centrifugation. The amount of SOMATULINE™ in the plasma samples was determined by a radioimmunoassay (RIA) technique that allowed the direct measurement without extraction of the peptide from the rat plasma.

Figure 5:
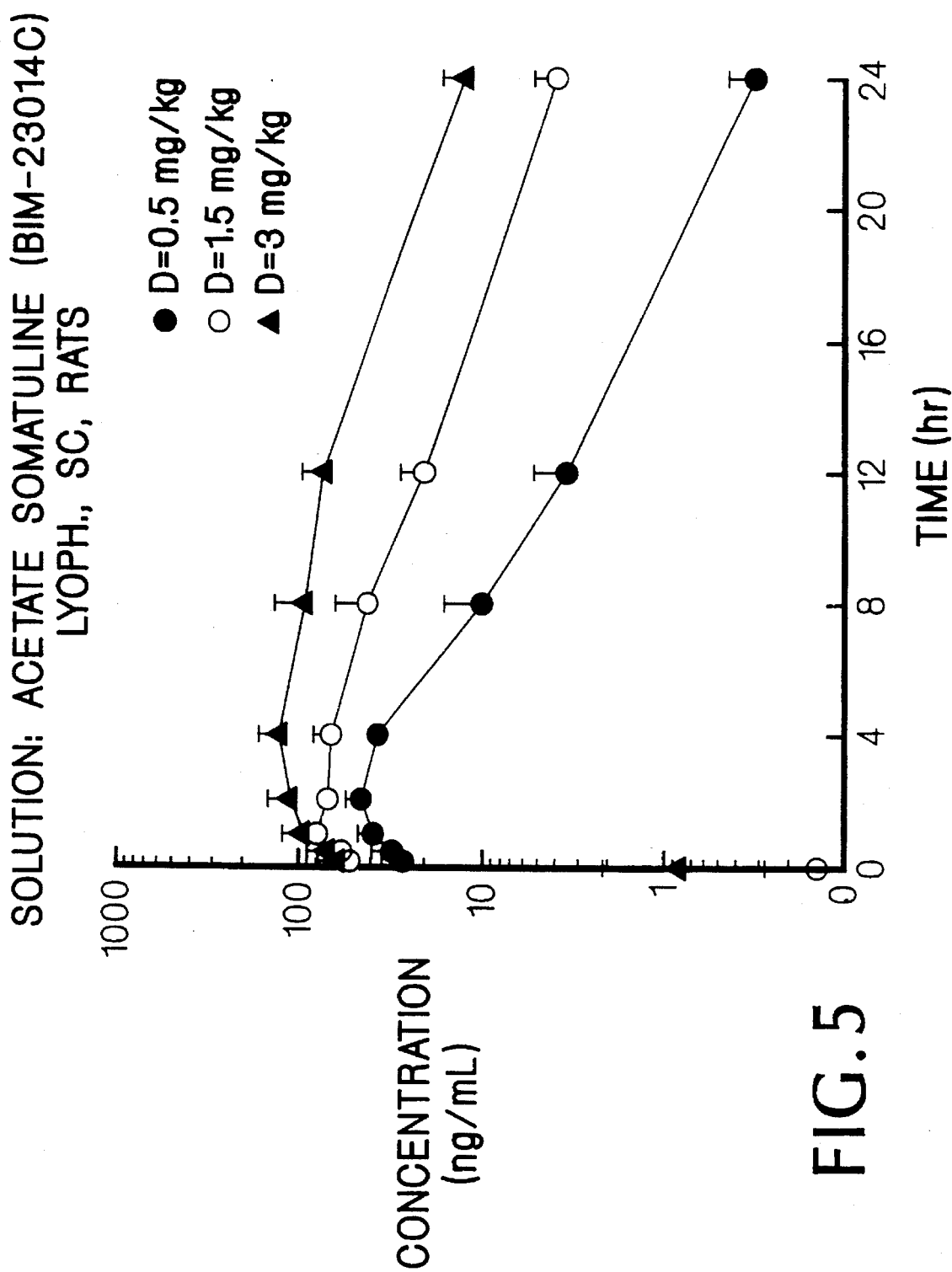
FIG. 5 is a graph comparing the blood level concentrations of a peptide from different dosages of a standard peptide solution over time in vivo in rats.

The same protocol was then repeated for SOMATULINE™ dosages of 1.5 and 3 mg/kg. The results (mean of data from six rats) are reproduced in Table II and shown in FIG. 5, and demonstrate an increase of maximum delivery rate and duration with increasing doses. As expected, the standard solutions result in a high initial peak of peptide release, the so-called "burst effect," that declines steadily over time.

TABLE II

| | PLASMA CONCENTRATION OF SOMATULINE ™ (ng/ml) | | |
|---|---|---|---|
| TIME (hr) | 0.5 mg/kg | 1.5 mg/kg | 3 mg/kg |
| 0.00 | 0.05 | 0.14 | 0.89 |
| 0.25 | 26.38 | 44.03 | 53.84 |
| 0.50 | 30.02 | 55.52 | 70.20 |
| 1.00 | 38.21 | 78.71 | 95.65 |
| 2.00 | 45.39 | 68.07 | 112.32 |
| 4.00 | 36.37 | 66.22 | 126.61 |
| 8.00 | 10.07 | 41.72 | 91.70 |
| 12.00 | 3.38 | 20.52 | 74.10 |
| 24.00 | 0.32 | 3.88 | 12.34 |

The maximum concentration ($C_{max}$) of the peptide was 45 ng/ml for the 0.5 mg/kg solution, 78 ng/ml for the 1.5 mg/kg solution, and 126 ng/ml for the 3 mg/kg solution.

Figure 6:
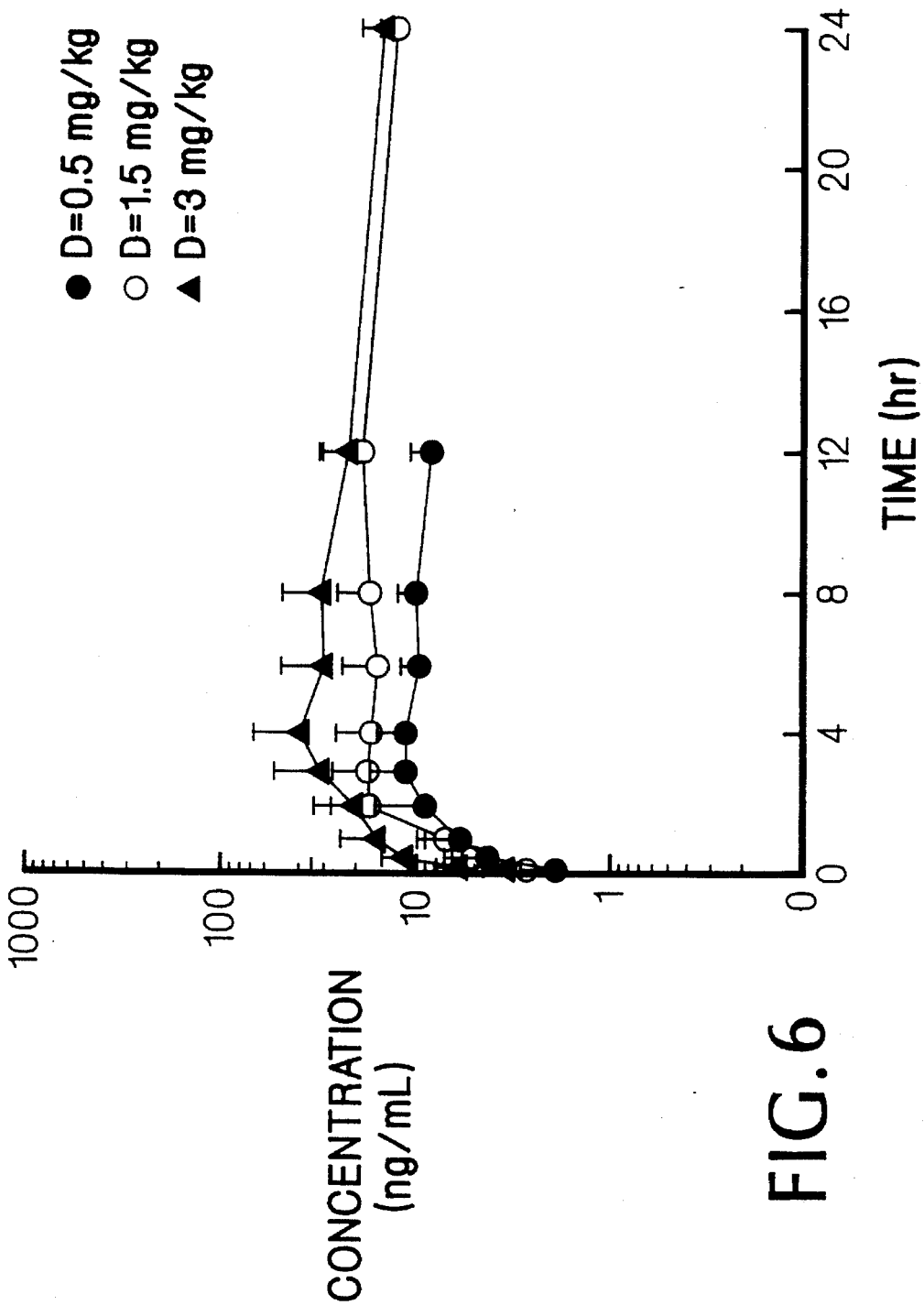
FIG. 6 is a graph comparing the blood level release profiles of different dosages of a solid peptide composition over time in vivo in rats.

Next, the same dosages of 100% SOMATULINE™ (0.5 mg/kg, 1.5 mg/kg, and 3 mg/kg) in solid form were administered to rats. The results (mean of data from four or five rats) are reproduced in Table III and shown in FIG. 6. The results show a sustained-release effect even at the smallest dose of 0.5 mg/kg. The initial burst effect of the solutions seen above is avoided by the solid compositions. For example, the $c_{max}$ for the solid 3.0 mg/kg composition is 39 ng/ml, compared to 126 ng/ml for the 3.0 mg/kg solution.

TABLE III

| | PLASMA CONCENTRATION OF SOMATULINE ™ (ng/ml) | | |
|---|---|---|---|
| TIME (hr) | 0.5 mg/kg | 1.5 mg/kg | 3 mg/kg |
| 0.00 | 0.00 | 0.00 | 0.00 |
| 0.08 | 1.89 | 2.60 | 3.38 |
| 0.25 | 3.49 | 4.23 | 7.24 |
| 0.50 | 3.97 | 5.43 | 11.85 |
| 1.00 | 6.05 | 7.04 | 17.01 |
| 2.00 | 9.09 | 17.51 | 22.49 |

TABLE III-continued

PLASMA CONCENTRATION OF SOMATULINE ™
(ng/ml)

| TIME (hr) | 0.5 mg/kg | 1.5 mg/kg | 3 mg/kg |
|---|---|---|---|
| 3.00 | 11.85 | 18.75 | 33.08 |
| 4.00 | 11.44 | 17.55 | 39.64 |
| 6.00 | 10.07 | 16.29 | 31.73 |
| 8.00 | 10.03 | 18.01 | 32.63 |
| 12.00 | 8.62 | 20.06 | 23.37 |
| 24.00 | not determined | 12.77 | 14.91 |

Example 11

Intramuscular Injection of Solid Compositions

Figure 7:
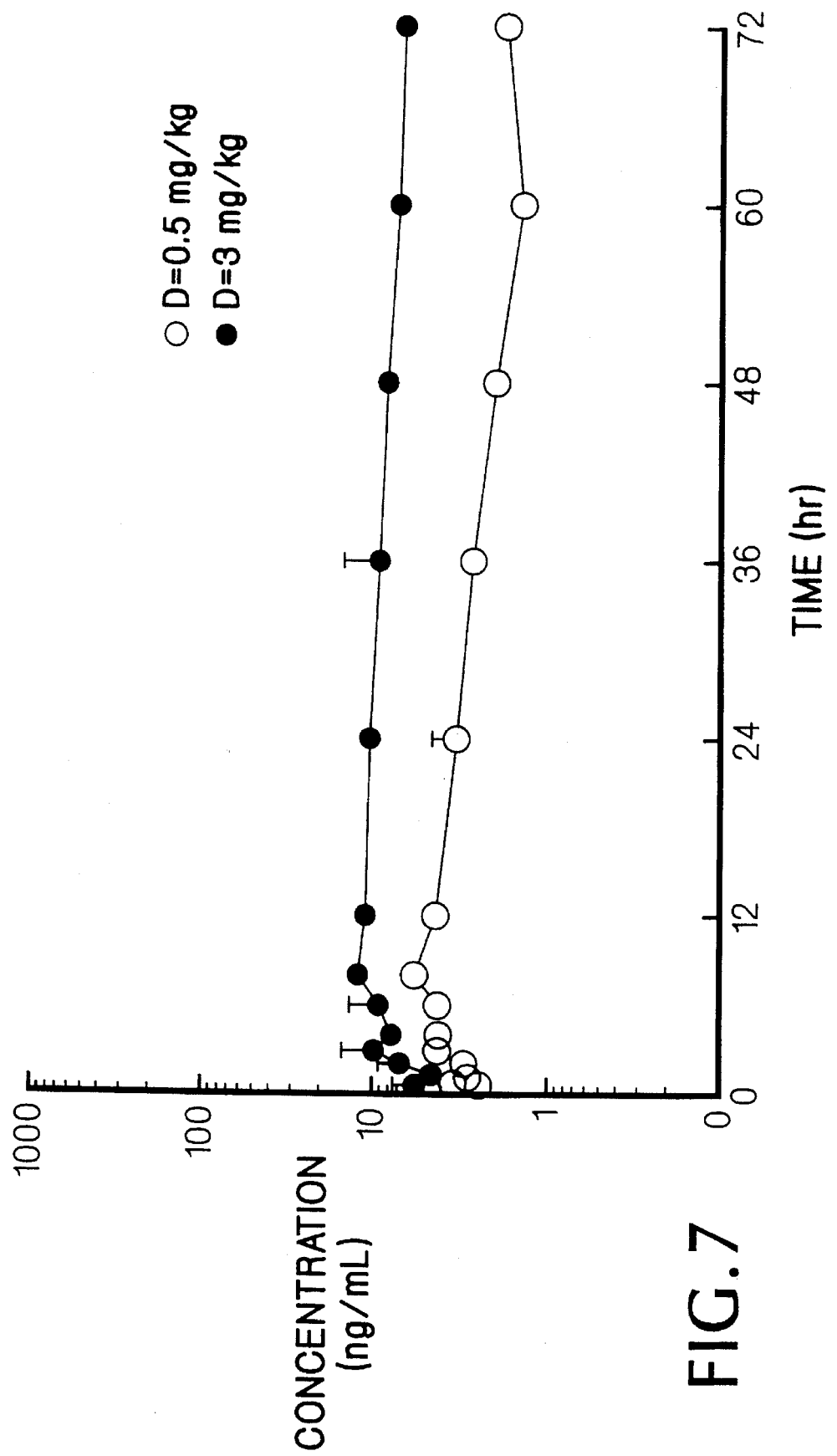
FIG. 7 is a graph comparing the blood level release profiles of two different dosages of a solid composition in vivo in rats.

The in vivo assay described above was also repeated on four rats using solid peptide compositions comprising 100% SOMATULINE™ at dosages of 0.5 mg/kg and 3 mg/kg. The compounds were administered intramuscularly. The results are depicted in FIG. 7, and show a sustained release over 72 hours, with the expected dosage effect, but without the burst effect seen with solutions.

Example 12

Subcataneous Injection of Solid Compositions

Figure 8:
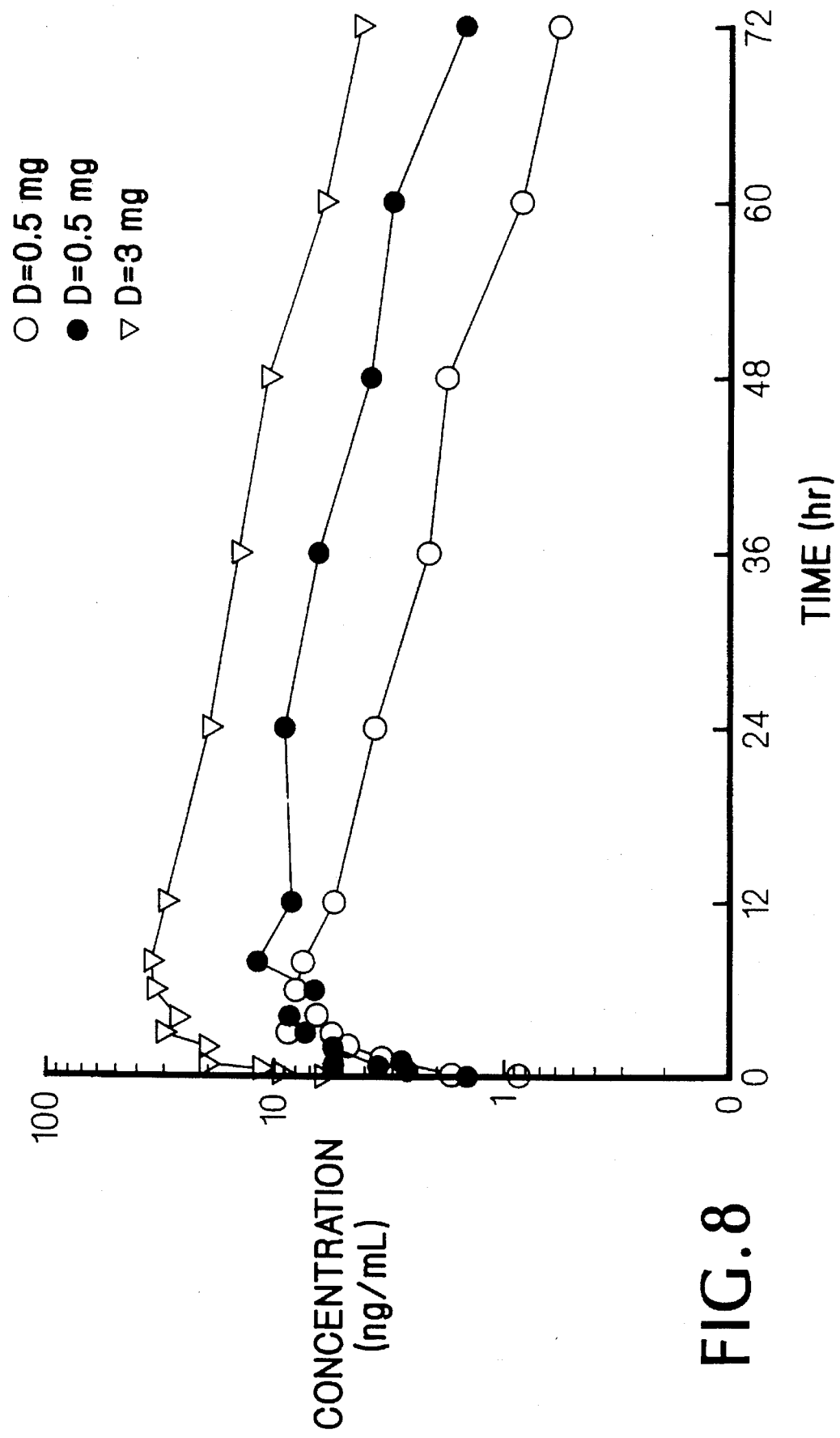
FIG. 8 is a graph comparing the blood level release profiles of three different dosages of a solid composition in vivo in rats.

The in vivo protocol described above was also repeated on six rats with solid compositions comprising 100% SOMATULINE™ at dosages of 0.5, 1.5, and 3 mg/kg. In this experiment, the compositions were administered subcutaneously. The results are shown in the graph of FIG. 8. As expected, a corresponding increase in plasma peptide concentration is seen with an increase in amount of drug ($C_{max}$ was 8.15 ng/ml for 0.5 mg/kg, 11.70 for 1.5 mg/kg, and 33.59 g/ml for 3 mg/kg). In addition, the burst effect of standard solutions is again diminished as was seen in Example 10 above.

Example 13

Comparative Studies in Dogs

The in vivo protocol described above was used to compare the pharmacokinetic parameters of peptide solutions and solid compositions in dogs. The delivery profile and release rate of a standard SOMATULINE™ solution was studied in five dogs after subcutaneous administration of a dosage of 84.8 μg/kg. For comparison, this same protocol was then followed with a solid composition comprising 100% SOMATULINE™ on the same five dogs at an equivalent dose of 100 μg/kg by subcutaneous injection.

Figure 9:
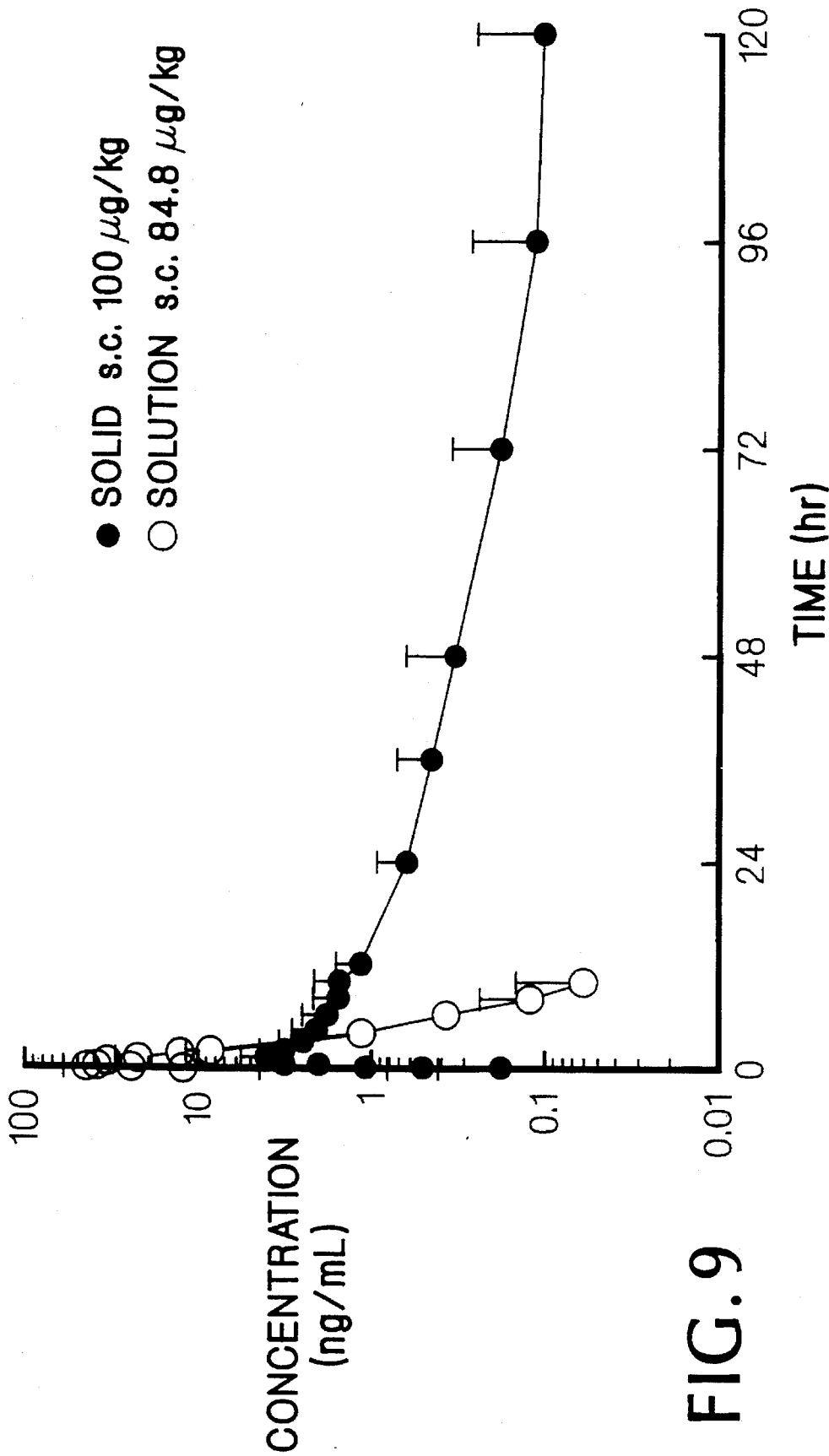
FIG. 9 is a graph comparing the blood level concentrations of a peptide from a standard peptide solution and a solid composition over time in vivo in dogs.

As shown in FIG. 9, the plot of plasma concentration versus time showed a classical release profile for the peptide solution (○), having a short release duration (10 hours) and a $C_{max}$ of 46.28 ng/ml (at 20 minutes). On the other hand, the solid composition (●) showed a dramatic difference in the pharmacokinetic results. As shown in FIG. 9, the $C_{max}$ was reduced to 3.56 ng/ml (at 1 hour), and the duration of peptide release of at least 0.1 ng/ml was increased more than ten times to at least 120 hours.

Figure 10:
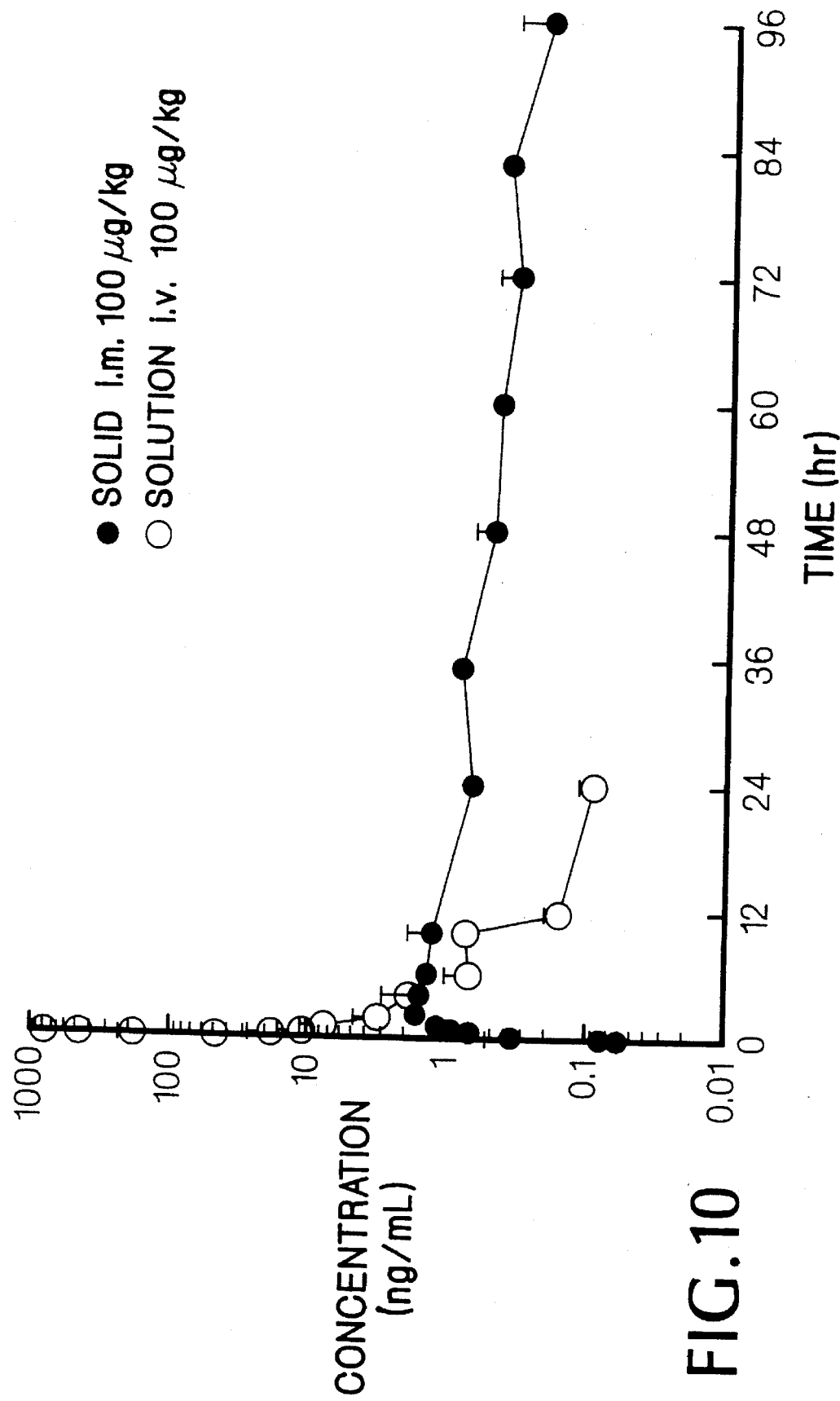
FIG. 10 is a graph comparing the blood level concentrations of a peptide from a standard peptide solution and a solid composition over time in vivo in dogs.

Similarly, an intravenous dosage of 100 μg/kg of a standard SOMATULINE™ solution (○) resulted in a rapid $C_{max}$ of about 807 ng/ml of plasma within just over 1 minute (FIG. 10). On the other hand, an intramuscular dosage of 100 μg/kg of a solid composition comprising 100% of the peptide (●) provided a dramatically different result. The solid composition provided a very low $C_{max}$ (1.69 ng/ml) at 2 hours, and a sustained release profile of over 96 hours (FIG. 10).

Figure 11:
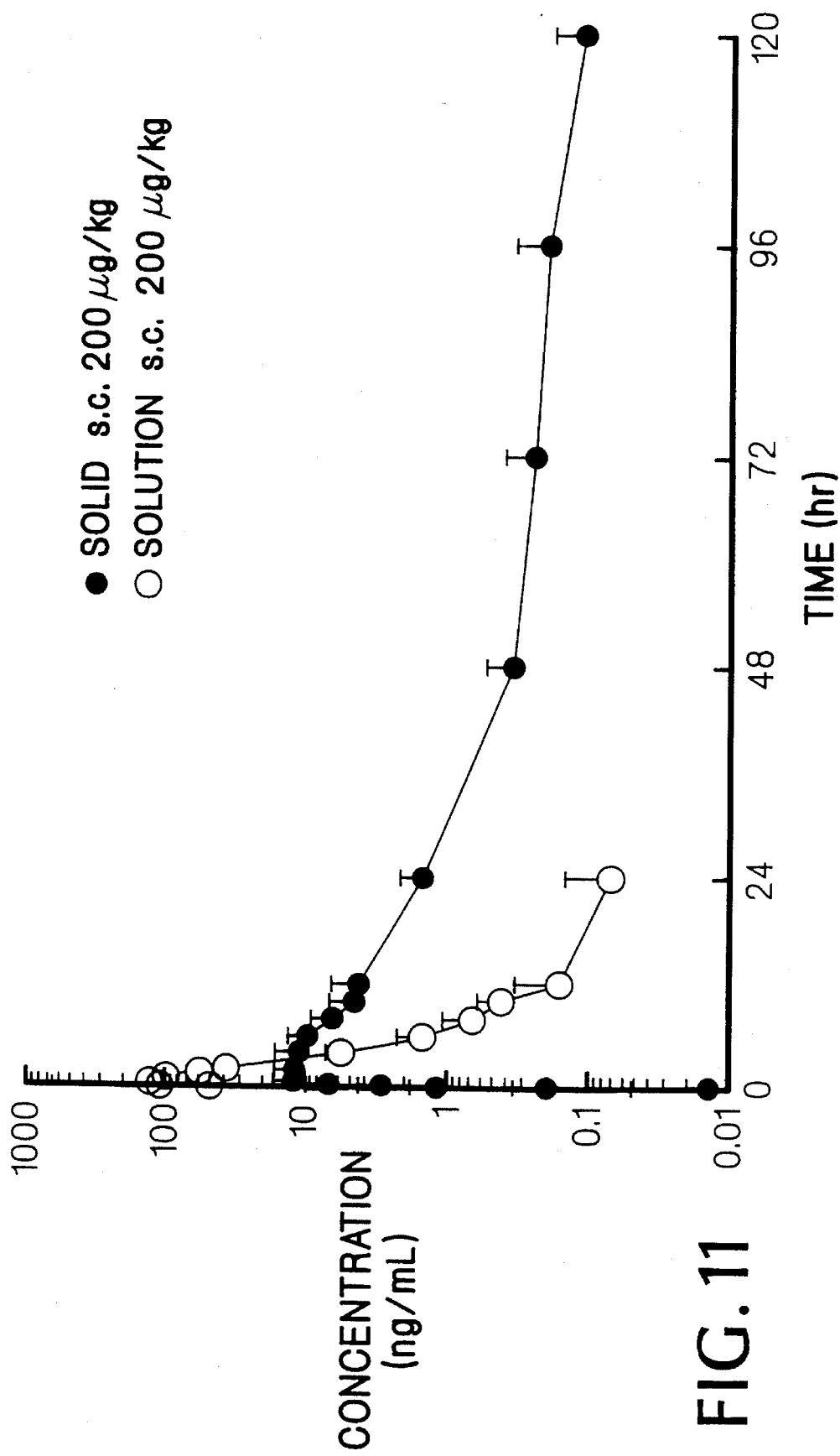
FIG. 11 is a graph comparing the blood level concentrations of a peptide from a standard peptide solution and a solid composition over time in vivo in dogs.

In another comparative study, six new dogs were injected subcutaneously with a standard solution of SOMATULINE™ at a dosage of 200 μg/kg. The results showed a $c_{max}$ of 125.96 ng/ml (at 20 minutes), and a duration less than 24 hours (FIG. 11, ○=solution). The same in vivo protocol was repeated on the same dogs with a solid composition (100% SOMATULINE™) at the same dosage (200 μg/kg) utilizing the same subcutaneous route of administration. As in the previous comparative tests, the solid composition results showed a completely different release profile, with a plasma $c_{max}$ of 13.26 ng/ml (at 1 hour), and a duration of peptide release of at least 0.1 ng/ml for more than 120 hours (FIG. 11, ● solid).

Example 14

Effect of Increased Dosage In Vivo

Figure 12:
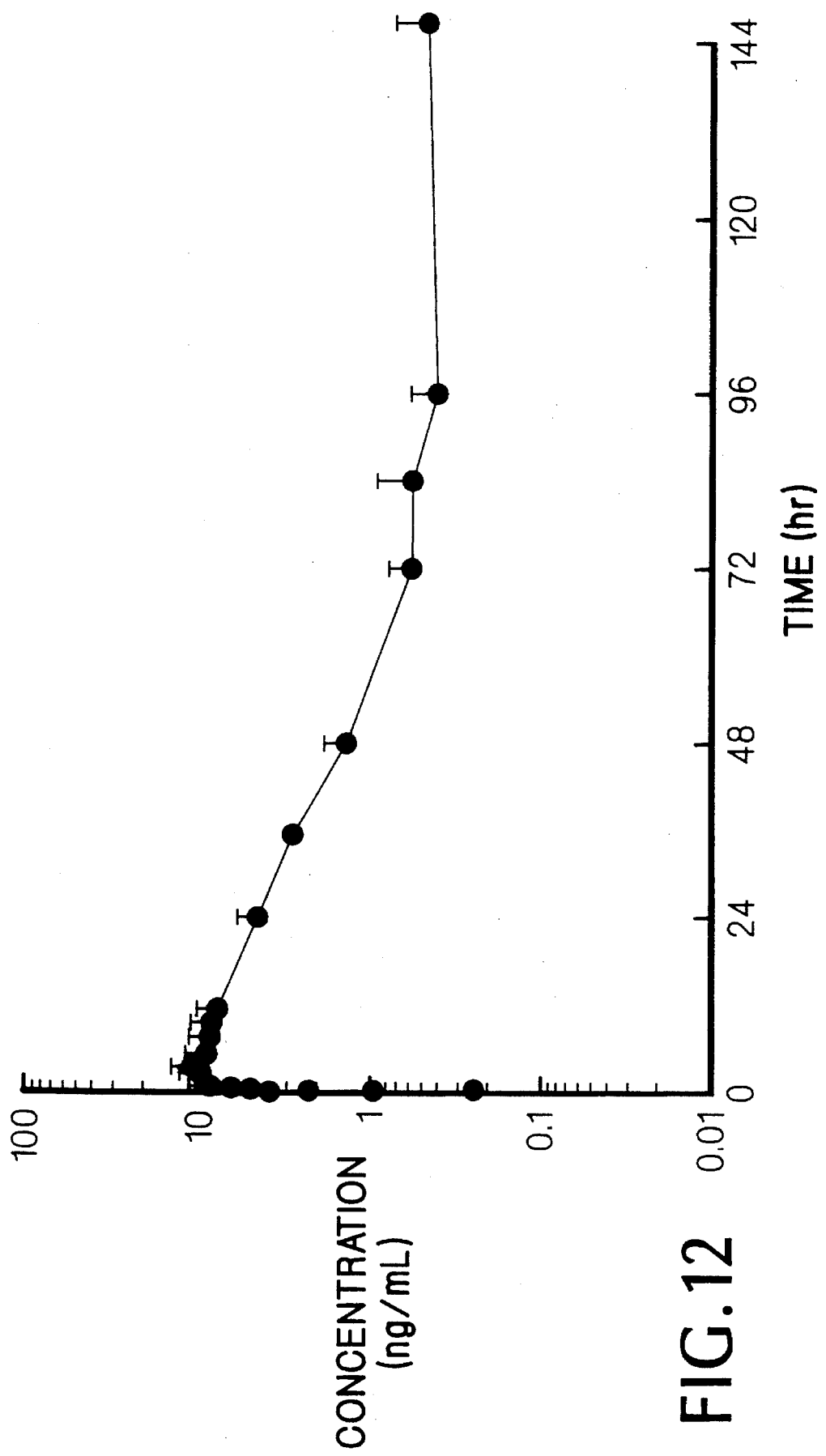
FIG. 12 is a graph showing the blood level release profile of a peptide resulting from the administration of a high dosage (500 µg/kg SOMATULINE™) of a solid composition to dogs.

The in vivo protocol described above was repeated with the same solid composition (100% SOMATULINE™) on the same dogs, but at a dosage 5 times higher (500 μg/kg) than in example 13, by subcutaneous administration. As in Example 13 above, the burst effect was still controlled with a plasma $C_{max}$ of 10.62 ng/ml (at 4 hours). In addition, the duration of release was increased and maintained for over 144 hours (FIG. 12).

Example 15

Effect of Surfactant In Vivo

Figure 13:
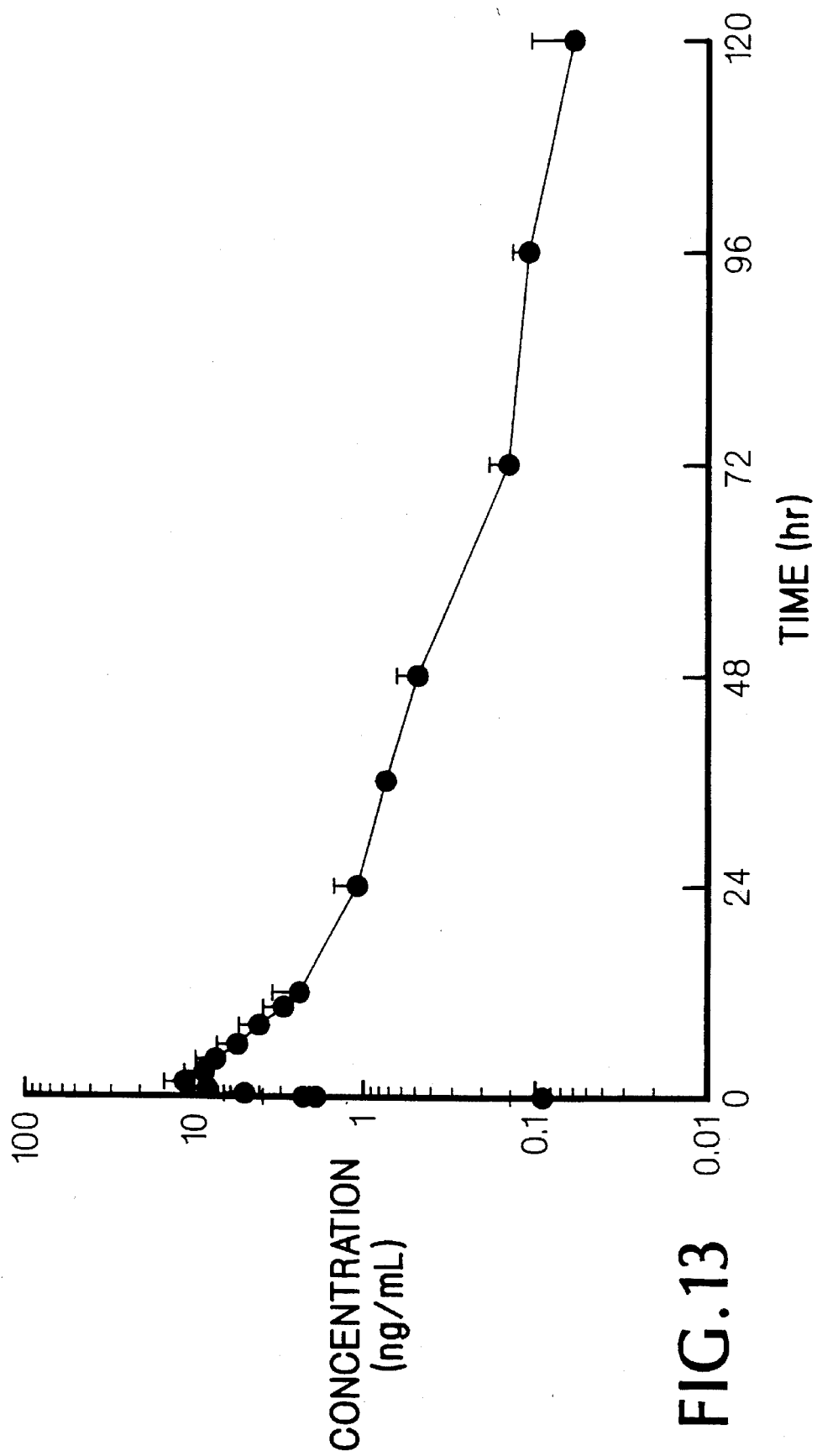
FIG. 13 is a graph showing the blood level release profile of a peptide resulting from the administration of a solid composition including a carrier to dogs.

The in vivo protocol described above was also repeated on the same dogs with a solid composition comprising SOMATULINE™ and the surfactant TWEEN® 80 (84% SOMATULINE™, 16% TWEEN® 80). The solid compositions were administered subcutaneously at a dosage of 100 μg/kg. As shown in FIG. 13 (as compared to FIG. 9), the surfactant somewhat accelerated the delivery of SOMATULINE™, i.e., increased the release rate and initial peak, and somewhat decreased the duration of release.

Example 16

Subcataneous Injection of Semisolid Suspensions

Figure 14:
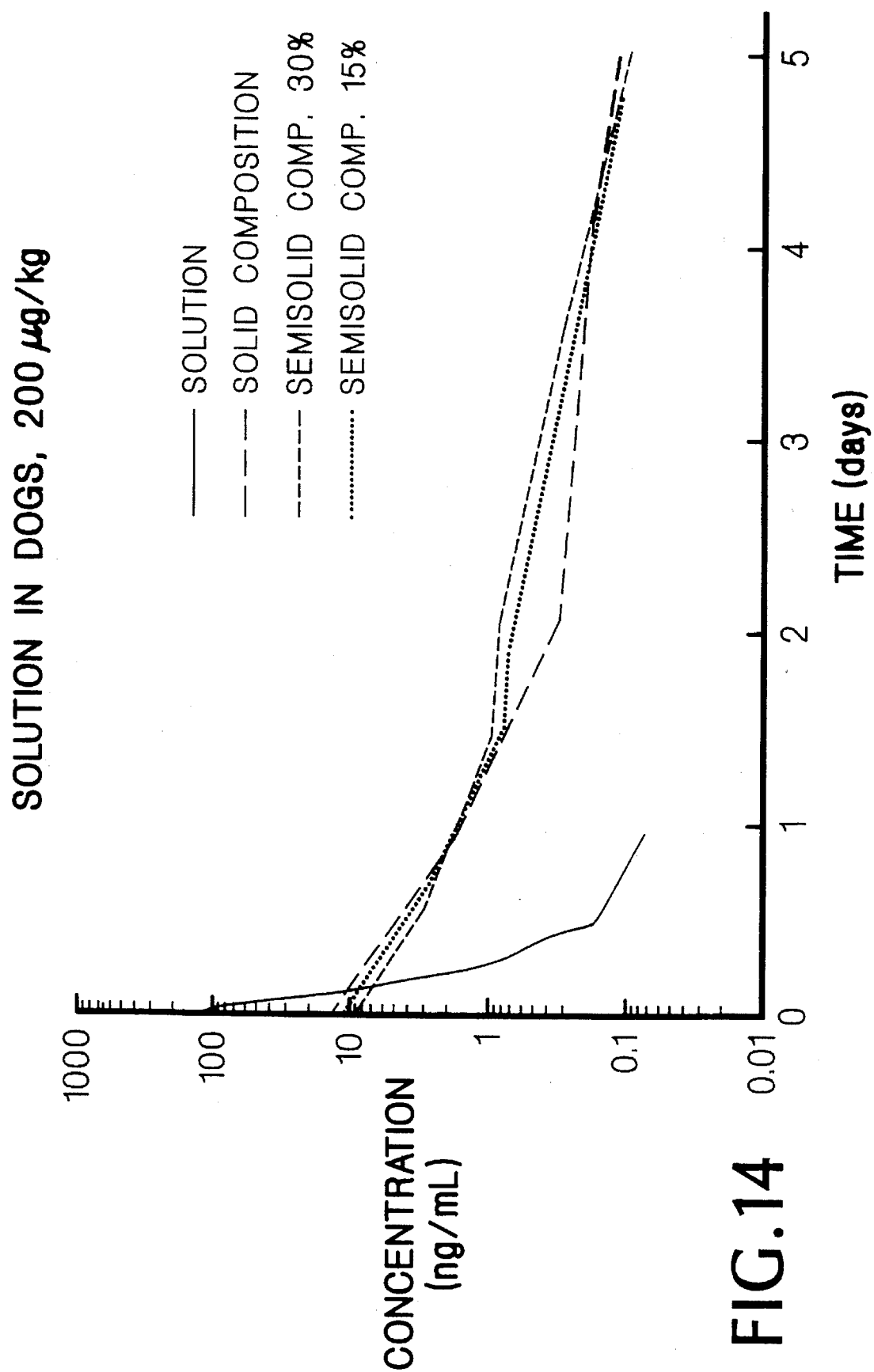
FIG. 14 is a graph comparing the blood level concentrations of a particular dosage of a peptide administered as a standard solution, a solid composition, or one of two semisolid suspensions to dogs.

The in vivo protocol described above was repeated on the same animals with semisolid suspensions of 30% SOMATULINE™ and 70% water, and 15% SOMATULINE™ and 85% water, at the same dosage of 200 μg/kg of peptide, utilizing subcutaneous administration. The results were not significantly different from the results obtained with the solid compositions at the same dosages as reported in Example 13. For example, the respective SOMATULINE™ plasma level at 24 hours was 1.74 ng/ml and 1.61 ng/ml for the semisolid compositions, and 1.51 ng/ml for the solid composition (FIG. 14). The semisolid compositions also had a higher release rate after two days, respectively, (0.9 and 0.87 ng/ml) than the solid composition (0.34 ng/ml). In both solid and semisolid compositions the release of the peptide was sustained for at least 120 hours, and the standard deviation was very small.

Example 17

High Dosage Injections

Figure 15:
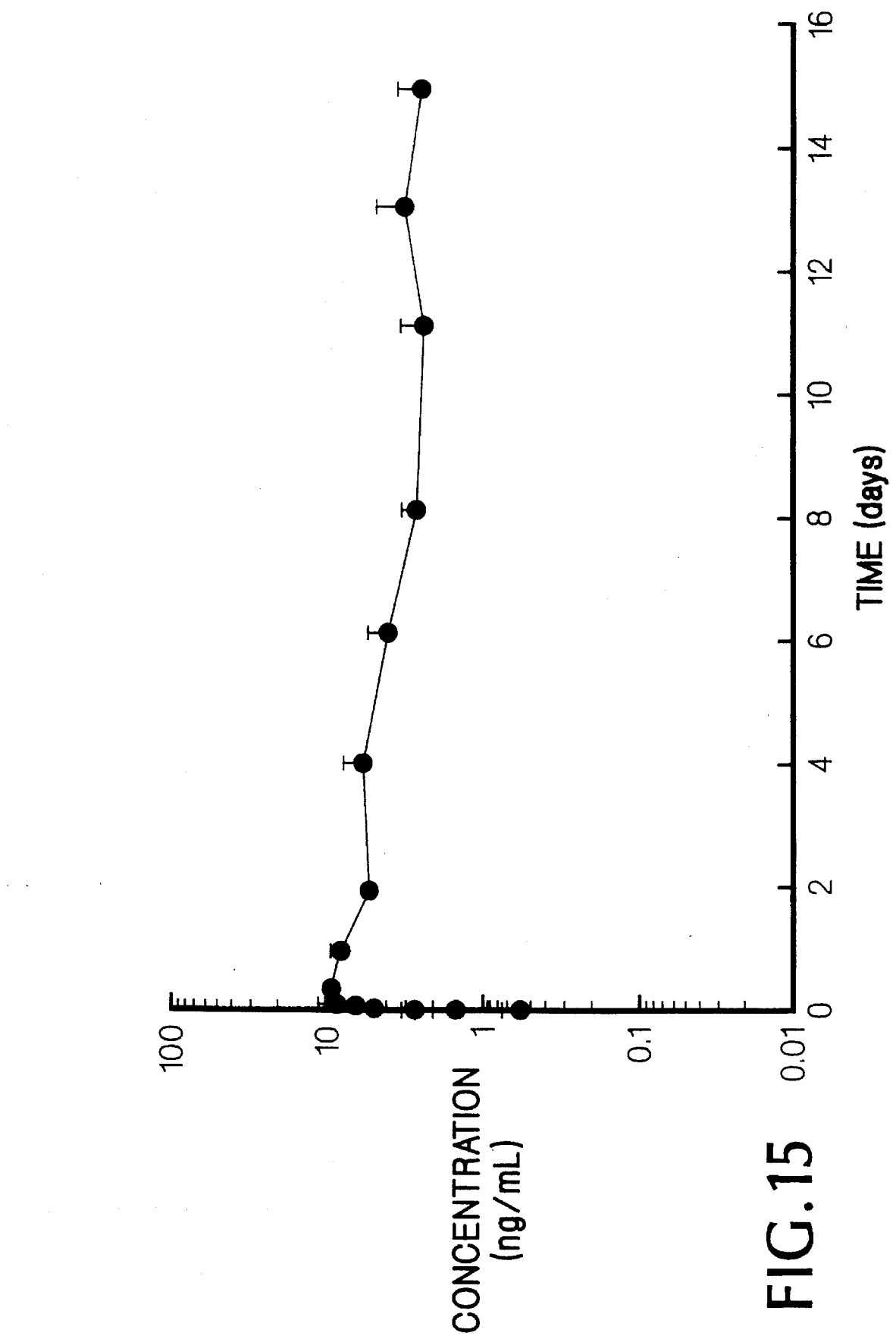
FIG. 15 is a graph showing the blood level release profile over 15 days of a peptide resulting from the administration of a semisolid suspension to dogs.

The in vivo protocol described above was repeated with a third set of six dogs. A high dose (3 mg/kg) of SOMATULINE™ was tested in an hydrated semisolid suspension (30% SOMATULINE™ and 70% water). The composition was administered intramuscularly. The results, depicted in FIG. 15, show a sustained release of the peptide even with this large dosage. The $C_{max}$ was still less than 10 ng/ml (9.25 ng/ml), and the duration was greatly increased with a maintained plasma concentration of greater than 2.4 ng/ml for more than 15 days.

The in vivo protocol described above was repeated in four dogs with a very high dosage, 6 mg/kg, of the same semisolid suspension described above (30% SOMATULINE™ and 70% water). This high dosage was tested to evaluate the limit of release rate control, e.g., to observe a possible so-called "escape phenomenon" in which delivery control is lost at very high dosages. Traditional sustained-release formulations have a maximum percentage of drug which can be compounded into the formulation, e.g., generally 15% for polylactic-glycolic acid (PLGA) microspheres. Once this maximum is reached, the formulation will lose its sustained-release characteristics and immediately release the drug.

Figure 16:
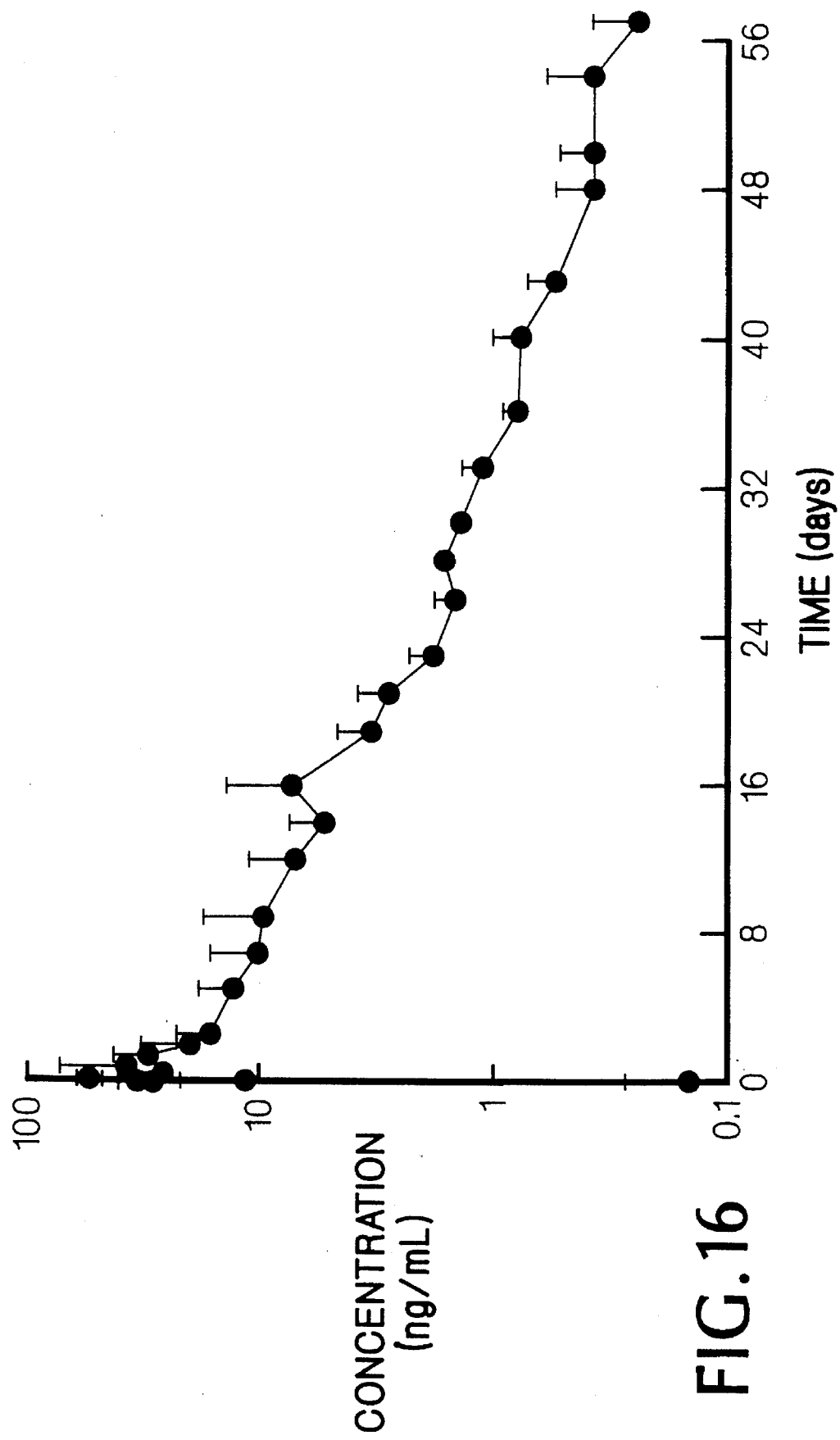
FIG. 16 is a graph showing the blood level release profile over 56 days of a peptide resulting from the administration of a high dosage (6 mg/kg) of a semisolid suspension to dogs.

The present experiment demonstrated that the plasma $C_{max}$ of SOMATULINE™ from the 6.0 mg/kg dosage was high, but within therapeutic bounds at about 52 ng/ml. Additionally, as shown in FIG. 16, rather than an escape phenomenon, the release of the peptide is controlled, i.e., sustained, but at a higher level, i.e., greater than about 10 ng/ml for days 1 to 7, about 1 to 10 ng/ml for days 8 to 33, and over 0.1 ng/ml for at least 56 days. As a comparison, a plasma level of greater than 7 ng/ml was maintained for only one day at a dosage of 3 mg/ml (FIG. 15), whereas this same level was maintained for 12 days at dosage of 6 mg/kg.

Example 18

Comparison of PLGA Microspheres and Semisolid Drug Compositions

Figure 17:
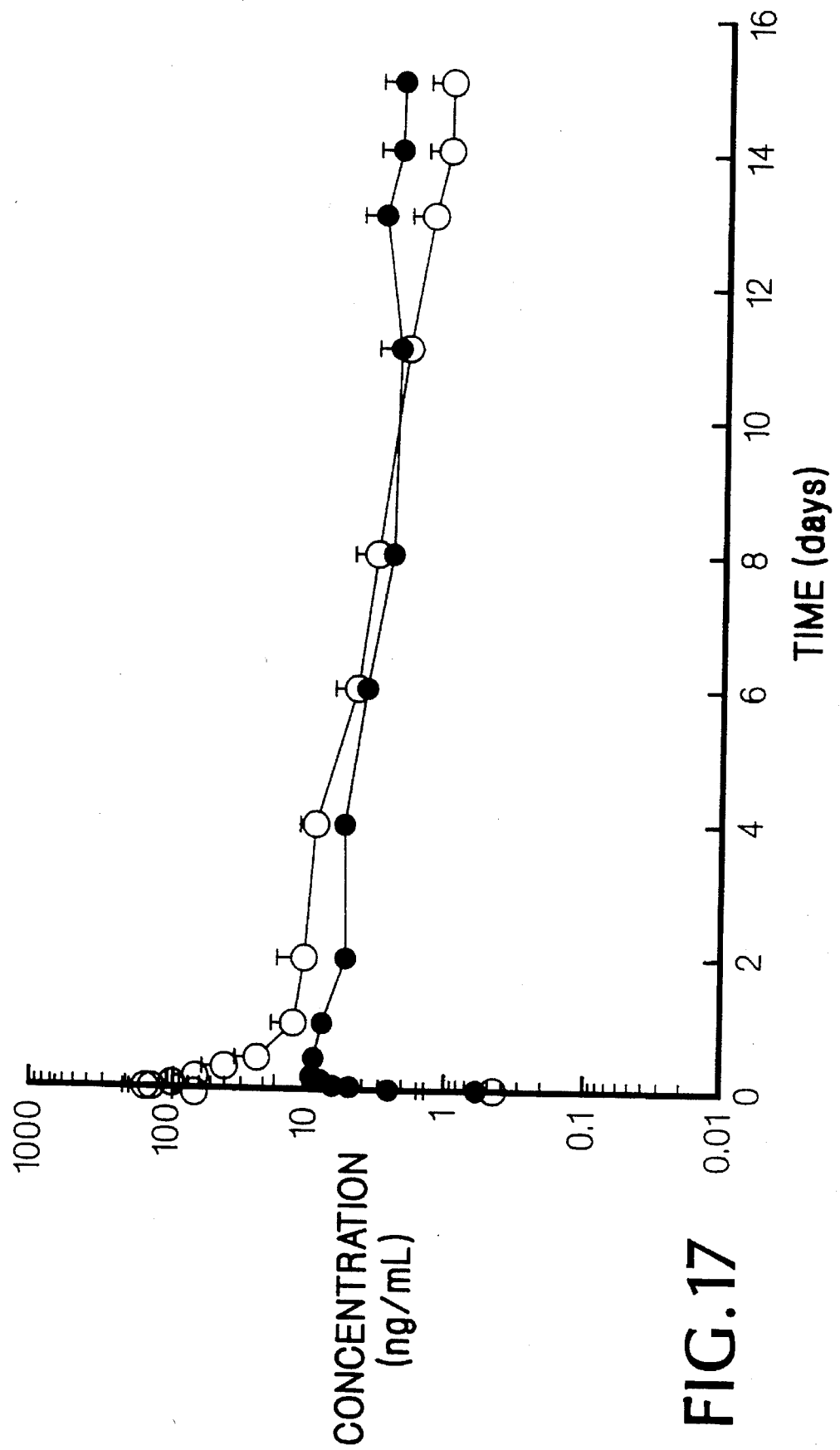
FIG. 17 is a graph comparing the blood level release profile over 15 days of a semisolid drug suspension and polylactic-glycolic microspheres when administered to dogs.

The in vivo protocol described above was used in six dogs to compare the delivery profiles and release rates of a semisolid SOMATULINE™ composition of the invention and a dosage of 30 mg of SOMATULINE™ loaded onto PLGA microspheres (Ipsen Biotech, Paris, France). This microsphere dosage is comparable to the dosage used in the first semisolid composition of Example 17, i.e. about 3.0 mg/kg. The graph of FIG. 17 shows the blood level profile of the semisolid composition (●) and the profile of the SOMATULINE™ loaded PLGA microspheres (○) over 15 days.

As shown in the graph, the semisolid composition provides an improved time and dosage control of the burst effect compared to the loaded microspheres (156 ng/ml after 30 minutes with the microspheres, and 2.6 ng/ml after 4 hours with the semisolid composition). Additionally, the semisolid composition provides a somewhat enhanced duration of release, having a release rate of 2.48 ng/ml at day 15, while the microspheres had a release rate of 1.09 ng/ml at day 15.

A Syringe Device

A syringe device for administering the semisolid suspensions is easily made using existing technologies. Such devices include a cylinder barrel, a needle, and a plunger assembly, all as found in standard syringes. The needle is a hollow needle with a maximum hollow aperture and a smooth internal surface, preferably with an internal surface of at least N6. The external diameter and length of the needle will be adapted to hypodermic or intramuscular use. The plunger stopper, which pushes the semisolid out of the barrel, through the needle, and into the patient, can be rubber or plastic, as currently used in disposable syringes. The plunger rod, which pushes the stopper, is an inexpensive and simple plastic accessory.

Figure 18:
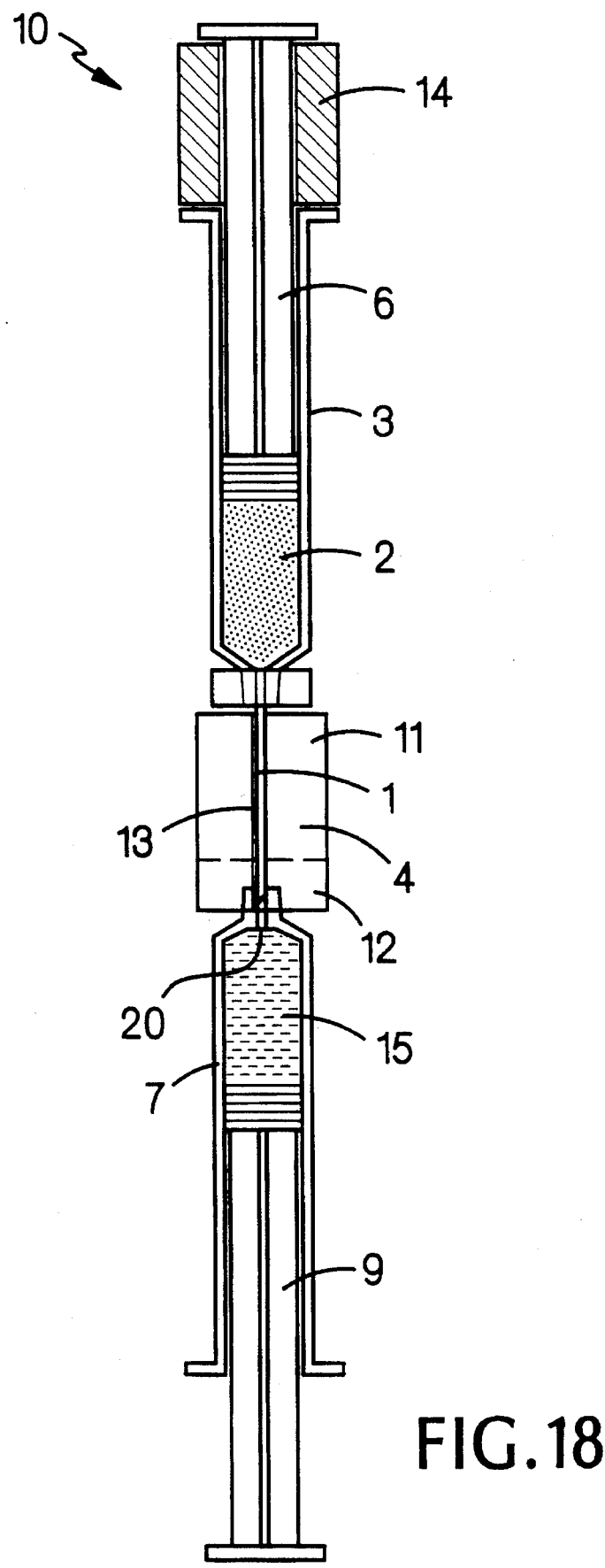
FIG. 18 is a side cross-sectional view of a syringe-like device used to deliver a semisolid pharmaceutical suspension.

FIG. 18 shows an injection device 10, which can be used to formulate and administer a semisolid composition. Injection device 10 includes hollow needle 1, which is attached to first syringe 3. Solid pharmaceutical composition 2, e.g., in the form of a lyophilized powder, is loaded into first syringe 3 and preferably stored under vacuum after insertion of a first plunger 6 into first syringe 3. Connector 4 comprises a first end 11, a second end 12, and a longitudinal bore 13 between first end 11 and second end 12. First end 11 is attached to first syringe 3 and second end 12 is attached to second syringe 7. Needle 1 is positioned within longitudinal bore 13. Connector 4 is preferably manufactured from plastic or metal. Sterile water 15 is loaded into second syringe 7. Barrier 20, positioned within second syringe 7, prevents the premature movement of water 15 from second syringe 7 into first syringe 3. Barrier 20 is preferably manufactured from an perforable material, e.g., a thin metal foil or a plastic film.

Barrier 20 is broken by force caused by the depression of plunger 9. Upon breakage of barrier 20, plunger 9 is further depressed, which will force water 15 from second syringe 7, through needle 1, and into first syringe 3. It is important to avoid separation of the barrier from the wall of the syringe, so that it does not enter the first syringe. The interaction of water 15 and solid drug composition 2 will cause the formation of a semisolid composition in first syringe 3. Both needle 1 and first syringe 3 are then separated from connector 4 and used to inject the semisolid composition into a patient in standard fashion. Plunger lock 14 prevents the depression of first plunger 6, which prevents movement of the dry, solid composition 2 into second syringe 7.

In another embodiment, the syringes are standard syringes, and are joined with a connector having a central bore, which may be lined with a plastic tube. No needle is initially attached to the first syringe, but is attached to the first syringe containing the peptide after water or other carrier has been introduced from the second syringe via the bore in the connector. In this embodiment, the barrier can be located within the bore or within the first syringe.

OTHER EMBODIMENTS

It is to be understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:

1. A method of administering a peptide to a patient and delivering the peptide continuously over an extended period of time of at least three days, said method comprising obtaining a solid pharmaceutical composition consisting essentially of a soluble, gelable peptide salt of said peptide and up to 30 percent, by weight, of a pharmaceutically acceptable, soluble, monomeric carrier, wherein said peptide salt and carrier are soluble in aqueous liquids, and parenterally administering said solid composition to the patient in one injection, wherein said solid composition automatically forms a gel after interaction with the patient's bodily fluids, said gel releasing said peptide continuously within the patient over an extended period of at least three days.

2. A method of claim 1, wherein said solid composition is administered intramuscularly, subcutaneously, or intradermally.

3. A method of claim 1, wherein said peptide is somatostatin or a somatostatin analog.

4. A method of claim 1, wherein said peptide is a soluble luteinizing hormone-releasing hormone (LHRH) analog.

5. A method of claim 1, wherein said peptide is growth hormone releasing factor (GRF), parathyroid hormone (PTH), parathyroid hormone related protein (PTHrp), calcitonin, or a soluble, biologically active analog of GRF, PTH, PTHrp, or calcitonin.

6. A method of claim 1, wherein said solid composition comprises no carrier.

7. A method of claim 1, wherein the carrier is selected from the group consisting of mannitol, sorbitol, or lactose.

8. A method of claim 1, wherein said solid composition is in the form of a cylinder with a diameter of less than 3 mm.

9. A method of claim 1, wherein said gel releases said peptide continuously over a period of at least 14 days.

10. A method of administering a peptide to a patient continuously over an extended period of time of at least three days, said method comprising obtaining a semisolid suspension consisting essentially of (1) a solid, soluble, gelable peptide salt of said peptide, and up to 30 percent, by weight, of a pharmaceutically acceptable, soluble, monomeric carrier, wherein said peptide salt and carrier are soluble in aqueous solvents; and (2) an aqueous solvent in an amount less than 50 percent of the amount of solvent required to dissolve said peptide salt and to provide said semisolid consistency; and parenterally administering said semisolid suspension to the patient in one injection, wherein said semisolid suspension automatically forms a gel after interaction with the patient's bodily fluids, said gel releasing said peptide continuously within the patient over an extended period of at least three days.

11. A method of claim 10, wherein said peptide is somatostatin or a somatostatin analog.

12. A method of claim 10, wherein said peptide is a soluble luteinizing hormone-releasing hormone (LHRH) analog.

13. A method of claim 10, wherein said peptide is growth hormone releasing factor (GRF), parathyroid hormone (PTH), parathyroid hormone related protein (PTHrp), calcitonin, or a soluble, biologically active analog of GRF, PTH, PTHrp, or calcitonin.

14. A method of claim 10, wherein said amount of solvent is less than 10 percent of the amount of solvent required to dissolve said peptide salt.

15. A sustained-release gel formed within a patient, said gel comprising a pharmaceutical composition consisting essentially of a soluble, gelable peptide salt and up to 30 percent, by weight, of a pharmaceutically acceptable, soluble, monomeric carrier, wherein said peptide salt and carrier are soluble in aqueous liquids, and one or more bodily fluids of the patient, wherein said peptide salt automatically forms said gel after interaction with said bodily fluids, and said gel releases said peptide continuously within the patient over a period of at least three days after formation.

16. A gel of claim 15, wherein said pharmaceutical composition is a solid.

17. A gel of claim 15, wherein said pharmaceutical composition further comprises a solvent in an amount less than 50 percent of the amount of solvent required to dissolve said peptide salt and to provide said pharmaceutical composition with a semisolid consistency.

18. A solid, non-particulate, sustained-release pharmaceutical composition for parenteral administration to a patient, said composition consisting essentially of (1) a soluble, gelable peptide salt, and (2) up to 30 percent, by weight, of a pharmaceutically acceptable, monomeric, soluble carrier, compounded into a solid cylindrical form, wherein said peptide salt and carrier are soluble in aqueous liquids and said solid composition automatically forms a gel after interaction with the patient's bodily fluids, said gel releasing said peptide continuously within the patient over an extended period of at least three days.

19. A composition of claim 18, wherein said peptide is selected from the group consisting of somatostatin or a somatostatin analog; a soluble, hydrophobic luteinizing hormone releasing hormone (LHRH) analog; growth hormone releasing factor (GRF); parathyroid hormone (PTH); parathyroid hormone related protein (PTHrp); calcitonin; or a soluble, biologically active analog of GRF, PTH, PTHrp, or calcitonin.

20. A semisolid, sustained-release pharmaceutical suspension for parenteral administration to a patient, said suspension consisting essentially of (1) a soluble, gelable peptide salt and up to 30 percent, by weight, of a pharmaceutically acceptable, soluble, monomeric carrier, wherein said peptide salt and said carrier are soluble in aqueous solvents; and (2) an aqueous solvent in an amount less than 50 percent of the amount of solvent required to dissolve said peptide salt and to provide said semisolid consistency of said suspension, wherein said semisolid suspension automatically forms a gel after interaction with the patient's bodily fluids, said gel releasing said peptide continuously within the patient over an extended period of at least three days.

21. A suspension of claim 20, wherein said amount of solvent is less than 10 percent of the amount of solvent required to dissolve said peptide salt.

22. A suspension of claim 20, wherein said peptide is selected from the group consisting of somatostatin or a somatostatin analog; a soluble, hydrophobic luteinizing hormone releasing hormone (LHRH) analog; growth hormone releasing factor (GRF); parathyroid hormone (PTH); parathyroid hormone related protein (PTHrp); calcitonin; or a soluble, biologically active analog of GRF, PTH, PTHrp, or calcitonin.

* * * * *